(12) United States Patent
Aragones et al.

(10) Patent No.: US 12,327,624 B2
(45) Date of Patent: *Jun. 10, 2025

(54) USER INTERFACE FOR REMOTE JOINT WORKOUT SESSION

(71) Applicant: NIKE, Inc., Beaverton, OR (US)

(72) Inventors: Teresa Aragones, Portland, OR (US); John M. Gordon, Lake Oswego, OR (US); Adriana Guerrero, Portland, OR (US); Christina S. Self, Portland, OR (US); Paul T. Winsper, West Linn, OR (US); Kristopher L. Homsi, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/737,887

(22) Filed: May 5, 2022

(65) Prior Publication Data
US 2022/0277824 A1    Sep. 1, 2022

Related U.S. Application Data

(63) Continuation of application No. 17/031,300, filed on Sep. 24, 2020, now Pat. No. 11,710,549, which is a
(Continued)

(51) Int. Cl.
*G16H 20/30* (2018.01)
*G09B 19/00* (2006.01)
(Continued)

(52) U.S. Cl.
CPC ......... *G16H 20/30* (2018.01); *G09B 19/0038* (2013.01); *G16H 20/60* (2018.01); *G16H 40/63* (2018.01); *G16H 40/67* (2018.01)

(58) Field of Classification Search
CPC ......... G16H 20/30; G16H 40/67; G16H 20/60
See application file for complete search history.

(56) References Cited

U.S. PATENT DOCUMENTS

| 3,145,484 A | 8/1964 | Bayley |
| 4,860,763 A | 8/1989 | Schminke |

(Continued)

FOREIGN PATENT DOCUMENTS

| CA | 2512601 A1 | 3/2002 |
| CN | 1415271 A | 5/2003 |

(Continued)

OTHER PUBLICATIONS

Machine translation for WO 2006111687 (Year: 2006).*
(Continued)

*Primary Examiner* — Malina D. Blaise
(74) *Attorney, Agent, or Firm* — Banner & Witcoff, Ltd.

(57) ABSTRACT

Example embodiments relate to a system, method, apparatus, and computer readable media configured to generate a multiple renditions of a user interface that is updated based upon athletic movements of two or more users remotely located from each other. The UI may be configured to simultaneously display energy expenditure values in real-time. In further embodiments, a joint energy expenditure values determined from multiple remote users may be simultaneously displayed.

24 Claims, 10 Drawing Sheets

Related U.S. Application Data continuation of application No. 15/857,320, filed on Dec. 28, 2017, now Pat. No. 10,825,561, which is a continuation of application No. 13/664,251, filed on Oct. 30, 2012, now Pat. No. 9,977,874, which is a continuation-in-part of application No. 13/324,812, filed on Dec. 13, 2011, now Pat. No. 9,852,271, which is a continuation-in-part of application No. 13/304,056, filed on Nov. 23, 2011, now Pat. No. 9,223,936, which is a continuation-in-part of application No. 13/290,359, filed on Nov. 7, 2011, now Pat. No. 9,283,429, said application No. 13/304,056 is a continuation-in-part of application No. 13/290,478, filed on Nov. 7, 2011, now Pat. No. 9,358,426, said application No. 13/324,812 is a continuation-in-part of application No. 13/304,064, filed on Nov. 23, 2011, now Pat. No. 9,457,256, which is a continuation-in-part of application No. 13/290,359, filed on Nov. 7, 2011, now Pat. No. 9,283,429, said application No. 13/324,812 is a continuation-in-part of application No. 13/290,359, filed on Nov. 7, 2011, now Pat. No. 9,283,429, said application No. 13/664,251 is a continuation-in-part of application No. 13/304,064, filed on Nov. 23, 2011, now Pat. No. 9,457,256.

(60) Provisional application No. 61/655,365, filed on Jun. 4, 2012, provisional application No. 61/433,792, filed on Jan. 18, 2011, provisional application No. 61/432,472, filed on Jan. 13, 2011, provisional application No. 61/422,511, filed on Dec. 13, 2010, provisional application No. 61/417,102, filed on Nov. 24, 2010, provisional application No. 61/410,777, filed on Nov. 5, 2010.

(51) Int. Cl.
  *G16H 20/60* (2018.01)
  *G16H 40/63* (2018.01)
  *G16H 40/67* (2018.01)

(56) References Cited

U.S. PATENT DOCUMENTS

| | | |
|---|---|---|
| 4,911,427 A | 3/1990 | Matsumoto et al. |
| 4,938,476 A | 7/1990 | Brunelle et al. |
| 5,184,295 A | 2/1993 | Mann |
| 5,277,197 A | 1/1994 | Church et al. |
| 5,288,078 A | 2/1994 | Capper et al. |
| 5,335,188 A | 8/1994 | Brisson |
| 5,354,317 A | 10/1994 | Alt |
| 5,375,610 A | 12/1994 | LaCourse et al. |
| 5,511,789 A | 4/1996 | Nakamura |
| 5,524,637 A | 6/1996 | Erickson |
| 5,527,239 A | 6/1996 | Abbondanza |
| 5,598,849 A | 2/1997 | Browne |
| 5,626,538 A | 5/1997 | Dalebout et al. |
| 5,655,316 A | 8/1997 | Huang |
| 5,667,459 A | 9/1997 | Su |
| 5,688,137 A | 11/1997 | Bustance |
| 5,791,351 A | 8/1998 | Curchod |
| 5,826,578 A | 10/1998 | Curchod |
| 5,836,770 A | 11/1998 | Powers |
| 5,846,086 A | 12/1998 | Bizzi et al. |
| 5,851,193 A | 12/1998 | Arikka et al. |
| 5,879,270 A | 3/1999 | Huish et al. |
| 5,888,172 A | 3/1999 | Andrus et al. |
| 5,904,484 A | 5/1999 | Burns |
| 5,913,727 A | 6/1999 | Ahdoot |
| 5,919,149 A | 7/1999 | Allum |
| 5,938,690 A | 8/1999 | Law et al. |
| 5,955,957 A | 9/1999 | Calabrese et al. |
| 5,976,083 A | 11/1999 | Richardson et al. |
| 6,026,335 A | 2/2000 | Atlas |
| 6,032,108 A | 2/2000 | Seiple et al. |
| 6,077,193 A | 6/2000 | Buhler et al. |
| 6,126,449 A | 10/2000 | Burns |
| 6,308,565 B1 | 10/2001 | French et al. |
| 6,316,934 B1 | 11/2001 | Amorai-Moriya et al. |
| 6,416,327 B1 | 7/2002 | Wittenbecher |
| 6,428,449 B1 | 8/2002 | Apseloff |
| 6,443,904 B2 | 9/2002 | Nissila |
| 6,458,060 B1 | 10/2002 | Watterson et al. |
| 6,493,652 B1 | 12/2002 | Ohlenbusch et al. |
| 6,516,222 B2 | 2/2003 | Fukuda |
| 6,527,674 B1 | 3/2003 | Clem |
| 6,585,622 B1 | 7/2003 | Shum et al. |
| 6,601,016 B1 | 7/2003 | Brown et al. |
| 6,607,493 B2 | 8/2003 | Song |
| 6,648,798 B2 | 11/2003 | Yoo |
| 6,656,091 B1 | 12/2003 | Abelbeck et al. |
| 6,663,491 B2 | 12/2003 | Watabe et al. |
| 6,672,991 B2 | 1/2004 | O'Malley |
| 6,687,535 B2 | 2/2004 | Hautala et al. |
| 6,736,759 B1 | 5/2004 | Stubbs et al. |
| 6,743,167 B2 | 6/2004 | Balkin et al. |
| 6,746,371 B1 | 6/2004 | Brown et al. |
| 6,749,432 B2 | 6/2004 | French et al. |
| 6,765,726 B2 | 7/2004 | French et al. |
| 6,786,848 B2 | 9/2004 | Yamashita et al. |
| 6,788,200 B1 | 9/2004 | Jamel et al. |
| 6,796,927 B2 | 9/2004 | Toyama |
| 6,817,979 B2 | 11/2004 | Nihtila |
| 6,820,025 B2 | 11/2004 | Bachmann et al. |
| 6,834,436 B2 | 12/2004 | Townsend et al. |
| 6,836,744 B1 | 12/2004 | Asphahani et al. |
| 6,856,852 B1 | 2/2005 | Bruinsma et al. |
| 6,858,006 B2 | 2/2005 | MacCarter et al. |
| 6,876,496 B2 | 4/2005 | French et al. |
| 6,902,513 B1 | 6/2005 | McClure |
| 6,997,852 B2 | 2/2006 | Watterson et al. |
| 7,018,211 B1 | 3/2006 | Birkholzer et al. |
| 7,054,678 B2 | 5/2006 | Dardik et al. |
| 7,074,168 B1 | 7/2006 | Farnes et al. |
| 7,076,291 B2 | 7/2006 | Pulkkinen et al. |
| 7,079,889 B2 | 7/2006 | Nakada |
| 7,089,216 B2 | 8/2006 | Van Overveld |
| 7,095,424 B2 | 8/2006 | Satoh et al. |
| 7,097,588 B2 | 8/2006 | Watterson et al. |
| 7,163,490 B2 | 1/2007 | Chen |
| 7,166,062 B1 | 1/2007 | Watterson et al. |
| 7,172,530 B1 | 2/2007 | Hercules |
| 7,192,401 B2 | 3/2007 | Saalasti et al. |
| 7,254,516 B2 | 8/2007 | Case, Jr. et al. |
| 7,265,666 B2 | 9/2007 | Daniel |
| 7,315,249 B2 | 1/2008 | Littell |
| 7,359,121 B2 | 4/2008 | French et al. |
| 7,433,805 B2 | 10/2008 | Vock et al. |
| 7,442,131 B2 | 10/2008 | Milana |
| 7,480,512 B2 | 1/2009 | Graham et al. |
| 7,493,232 B1 | 2/2009 | Surina |
| 7,497,807 B2 | 3/2009 | Neff et al. |
| 7,497,812 B2 | 3/2009 | Neff et al. |
| 7,556,590 B2 | 7/2009 | Watterson et al. |
| 7,559,877 B2 | 7/2009 | Parks et al. |
| 7,602,301 B1 | 10/2009 | Stirling et al. |
| 7,628,730 B1 | 12/2009 | Watterson et al. |
| 7,676,332 B2 | 3/2010 | Damen |
| 7,699,753 B2 | 4/2010 | Daikeler et al. |
| 7,717,858 B2 | 5/2010 | Massad |
| 7,722,502 B2 | 5/2010 | Holkkola |
| 7,736,272 B2 | 6/2010 | Martens |
| 7,771,293 B1 | 8/2010 | Vann |
| 7,771,320 B2 | 8/2010 | Riley et al. |
| 7,782,358 B2 | 8/2010 | Nieminen et al. |
| 7,783,347 B2 | 8/2010 | Abourizk et al. |
| 7,789,800 B1 | 9/2010 | Watterson et al. |
| 7,810,392 B2 | 10/2010 | Kitagawa |
| 7,815,508 B2 | 10/2010 | Dohta |
| 7,821,407 B2 | 10/2010 | Shears et al. |
| 7,825,815 B2 | 11/2010 | Shears et al. |

(56) References Cited

U.S. PATENT DOCUMENTS

| | | |
|---|---|---|
| 7,846,067 B2 | 12/2010 | Hanoun |
| 7,846,069 B2 | 12/2010 | Martens |
| 7,850,514 B2 | 12/2010 | Weber |
| 7,857,708 B2 | 12/2010 | Ueda et al. |
| 7,894,849 B2 | 2/2011 | Kass et al. |
| 7,927,253 B2 | 4/2011 | Vincent et al. |
| 7,967,728 B2 | 6/2011 | Zavadsky et al. |
| 7,978,081 B2 | 7/2011 | Shears et al. |
| 7,978,217 B2 | 7/2011 | Camhi |
| 7,985,164 B2 | 7/2011 | Ashby |
| 7,988,647 B2 | 8/2011 | Bunn et al. |
| 8,012,064 B2 | 9/2011 | Martens |
| 8,029,411 B2 | 10/2011 | Johnson |
| 8,038,549 B2 | 10/2011 | Vann |
| 8,038,578 B2 | 10/2011 | Olrik et al. |
| 8,083,643 B2 | 12/2011 | Ng et al. |
| 8,109,858 B2 | 2/2012 | Redmann |
| 8,118,710 B2 | 2/2012 | Weinman et al. |
| 8,177,260 B2 | 5/2012 | Tropper et al. |
| 8,212,136 B2 | 7/2012 | Shirai et al. |
| 8,230,367 B2 * | 7/2012 | Bell ............ G06V 40/20 463/32 |
| 8,235,870 B2 * | 8/2012 | Hamilton ........ A63B 21/4037 482/148 |
| 8,253,586 B1 | 8/2012 | Matak |
| 8,269,826 B2 * | 9/2012 | Nieminen .......... A61B 5/1127 600/592 |
| 8,284,157 B2 * | 10/2012 | Markovic ............ G06F 3/017 715/706 |
| 8,284,847 B2 * | 10/2012 | Adermann ........... H04N 7/181 725/107 |
| 8,346,524 B2 | 1/2013 | Turgiss et al. |
| 8,409,057 B2 * | 4/2013 | Martens ............... A63F 13/80 482/8 |
| 8,435,177 B2 * | 5/2013 | Lanfermann ...... A63B 24/0006 482/148 |
| 8,460,199 B2 * | 6/2013 | Rulkov ............... A61B 5/681 600/301 |
| 8,465,108 B2 | 6/2013 | Markovic et al. |
| 8,503,086 B2 * | 8/2013 | French ............ A63B 24/0062 73/379.04 |
| 8,523,667 B2 * | 9/2013 | Clavin ............. G06V 40/103 715/810 |
| 8,568,277 B2 * | 10/2013 | Johnson ............ G06F 16/284 482/901 |
| 8,568,330 B2 * | 10/2013 | Mollicone ........... A61B 5/024 600/508 |
| 8,589,114 B2 * | 11/2013 | Papadourakis .... A63B 69/3632 473/223 |
| 8,602,988 B2 * | 12/2013 | Hunt ................ A63B 24/0075 600/300 |
| 8,616,989 B2 * | 12/2013 | Bentley ............. A63F 13/213 473/215 |
| 8,676,541 B2 * | 3/2014 | Schrock ........... A63B 24/0062 702/188 |
| 8,702,485 B2 * | 4/2014 | Flury .................. A63F 13/46 463/7 |
| 8,758,201 B2 * | 6/2014 | Ashby ................. A63B 22/00 482/901 |
| 8,784,270 B2 | 7/2014 | Ashby et al. |
| 8,784,307 B1 * | 7/2014 | Groteke ............ A61B 5/4528 600/300 |
| 8,812,428 B2 * | 8/2014 | Mollicone ........... G16Z 99/00 600/300 |
| 8,814,755 B2 | 8/2014 | Ellis et al. |
| 8,845,496 B2 | 9/2014 | Arrasvuori et al. |
| 8,854,304 B2 * | 10/2014 | Nishimoto .......... A63F 13/213 345/157 |
| 8,858,400 B2 | 10/2014 | Johnson |
| 8,861,091 B2 | 10/2014 | French et al. |
| 8,892,219 B2 * | 11/2014 | Pryor ................. B60R 11/02 482/901 |
| 8,911,328 B2 * | 12/2014 | Alessandri ........... G16H 20/30 482/901 |
| 8,928,484 B2 * | 1/2015 | Chang .............. A61B 5/0002 340/573.7 |
| 9,008,973 B2 * | 4/2015 | French ............ A63B 24/0087 600/595 |
| 9,078,585 B2 * | 7/2015 | Miyazaki ............ A61B 5/389 |
| 9,141,759 B2 * | 9/2015 | Burich ............ A63B 24/0062 |
| 9,149,222 B1 * | 10/2015 | Zets ................ A61B 5/4023 |
| 9,154,739 B1 * | 10/2015 | Nicolaou ............... H04N 7/18 |
| 9,317,660 B2 * | 4/2016 | Burich ............ A63B 24/0062 |
| 9,329,053 B2 * | 5/2016 | Lakovic ............. G04G 17/045 |
| 9,390,229 B1 | 7/2016 | Kahn et al. |
| 9,504,414 B2 | 11/2016 | Coza et al. |
| 9,545,541 B2 * | 1/2017 | Aragones ............ G16H 40/63 |
| 9,630,059 B2 | 4/2017 | Burich et al. |
| 10,610,761 B1 | 4/2020 | Matak et al. |
| 2001/0034014 A1 | 10/2001 | Nishimoto et al. |
| 2002/0019258 A1 | 2/2002 | Kim et al. |
| 2002/0077219 A1 | 6/2002 | Cohen et al. |
| 2002/0116147 A1 | 8/2002 | Vock et al. |
| 2002/0160883 A1 | 10/2002 | Dugan |
| 2002/0183961 A1 | 12/2002 | French et al. |
| 2003/0040348 A1 | 2/2003 | Martens |
| 2003/0054327 A1 | 3/2003 | Evensen |
| 2003/0065561 A1 | 4/2003 | Brown et al. |
| 2003/0077556 A1 | 4/2003 | French et al. |
| 2003/0134714 A1 | 7/2003 | Oishi et al. |
| 2003/0190062 A1 | 10/2003 | Noro et al. |
| 2003/0214408 A1 | 11/2003 | Grajales et al. |
| 2003/0228033 A1 | 12/2003 | Daniel et al. |
| 2003/0228628 A1 | 12/2003 | Powell |
| 2004/0087366 A1 | 5/2004 | Shum et al. |
| 2004/0102931 A1 | 5/2004 | Ellis et al. |
| 2004/0112151 A1 | 6/2004 | Maxwell et al. |
| 2004/0162194 A1 | 8/2004 | Habing |
| 2004/0219498 A1 | 11/2004 | Davidson |
| 2004/0220856 A1 | 11/2004 | Moore |
| 2004/0255490 A1 | 12/2004 | Wan et al. |
| 2005/0001728 A1 | 1/2005 | Appelt et al. |
| 2005/0038679 A1 | 2/2005 | Short |
| 2005/0070809 A1 | 3/2005 | Acres |
| 2005/0079905 A1 | 4/2005 | Martens |
| 2005/0085348 A1 | 4/2005 | Kiefer et al. |
| 2005/0101845 A1 | 5/2005 | Nihtila |
| 2005/0101887 A1 | 5/2005 | Stark et al. |
| 2005/0107723 A1 | 5/2005 | Wehman et al. |
| 2005/0113650 A1 | 5/2005 | Pacione et al. |
| 2005/0113652 A1 | 5/2005 | Stark et al. |
| 2005/0172311 A1 | 8/2005 | Hjelt et al. |
| 2005/0182341 A1 | 8/2005 | Katayama et al. |
| 2005/0196737 A1 | 9/2005 | Mann |
| 2005/0209050 A1 | 9/2005 | Bartels |
| 2005/0223799 A1 | 10/2005 | Murphy |
| 2005/0233861 A1 | 10/2005 | Hickman et al. |
| 2005/0234307 A1 | 10/2005 | Heinonen et al. |
| 2005/0239026 A1 | 10/2005 | Suzuki et al. |
| 2005/0250458 A1 | 11/2005 | Graham et al. |
| 2005/0272517 A1 | 12/2005 | Funk et al. |
| 2005/0272564 A1 | 12/2005 | Pyles et al. |
| 2006/0003872 A1 | 1/2006 | Chiles et al. |
| 2006/0025282 A1 | 2/2006 | Redmann |
| 2006/0040793 A1 | 2/2006 | Martens |
| 2006/0079800 A1 | 4/2006 | Martikka et al. |
| 2006/0111944 A1 | 5/2006 | Sirmans et al. |
| 2006/0136173 A1 | 6/2006 | Case et al. |
| 2006/0166737 A1 | 7/2006 | Bentley |
| 2006/0173070 A1 | 8/2006 | Murase et al. |
| 2006/0183602 A1 | 8/2006 | Astilean |
| 2006/0189440 A1 | 8/2006 | Gravagne |
| 2006/0205569 A1 | 9/2006 | Watterson et al. |
| 2006/0228681 A1 | 10/2006 | Clarke |
| 2006/0229170 A1 | 10/2006 | Ozawa et al. |
| 2006/0241521 A1 | 10/2006 | Cohen |
| 2006/0247070 A1 | 11/2006 | Funk et al. |
| 2006/0252617 A1 | 11/2006 | Gill |
| 2006/0262120 A1 | 11/2006 | Rosenberg |
| 2006/0282021 A1 | 12/2006 | DeVaul et al. |
| 2006/0284979 A1 | 12/2006 | Clarkson |

(56) References Cited

U.S. PATENT DOCUMENTS

| | | |
|---|---|---|
| 2006/0293617 A1 | 12/2006 | Einav et al. |
| 2007/0032345 A1 | 2/2007 | Padmanabhan et al. |
| 2007/0050715 A1 | 3/2007 | Behar |
| 2007/0118406 A1 | 5/2007 | Killin et al. |
| 2007/0155588 A1 | 7/2007 | Stark et al. |
| 2007/0177024 A1 | 8/2007 | Camhi |
| 2007/0213178 A1 | 9/2007 | Lemmela |
| 2007/0232453 A1 | 10/2007 | Hanoun |
| 2007/0232455 A1 | 10/2007 | Hanoun |
| 2007/0239479 A1 | 10/2007 | Arrasvuori et al. |
| 2007/0270214 A1 | 11/2007 | Bentley |
| 2007/0271065 A1 | 11/2007 | Gupta et al. |
| 2007/0272011 A1 | 11/2007 | Chapa et al. |
| 2008/0033581 A1 | 2/2008 | Doshi et al. |
| 2008/0077620 A1 | 3/2008 | Gilley et al. |
| 2008/0096726 A1 | 4/2008 | Riley et al. |
| 2008/0146302 A1 | 6/2008 | Olsen et al. |
| 2008/0161733 A1 | 7/2008 | Einav et al. |
| 2008/0176655 A1 | 7/2008 | James et al. |
| 2008/0189291 A1 | 8/2008 | Hsu |
| 2008/0191864 A1 | 8/2008 | Wolfson |
| 2008/0200312 A1 | 8/2008 | Tagliabue |
| 2008/0207401 A1 | 8/2008 | Harding et al. |
| 2008/0212032 A1 | 9/2008 | Seiller et al. |
| 2008/0221487 A1 | 9/2008 | Zohar et al. |
| 2008/0246629 A1 | 10/2008 | Tsui et al. |
| 2008/0254866 A1 | 10/2008 | Young et al. |
| 2008/0267444 A1 | 10/2008 | Simons-Nikolova et al. |
| 2008/0269016 A1 | 10/2008 | Ungari et al. |
| 2008/0281550 A1 | 11/2008 | Hogle et al. |
| 2009/0023555 A1 | 1/2009 | Raymond |
| 2009/0042695 A1 | 2/2009 | Chien et al. |
| 2009/0044429 A1 | 2/2009 | Cook et al. |
| 2009/0062092 A1 | 3/2009 | Mortimer et al. |
| 2009/0069722 A1 | 3/2009 | Flaction et al. |
| 2009/0098519 A1 | 4/2009 | Byerly |
| 2009/0118100 A1 | 5/2009 | Oliver et al. |
| 2009/0144369 A1 | 6/2009 | Brown |
| 2009/0149299 A1 | 6/2009 | Tchao et al. |
| 2009/0150178 A1 | 6/2009 | Sutton et al. |
| 2009/0171614 A1 | 7/2009 | Damen |
| 2009/0209358 A1 | 8/2009 | Niegowski |
| 2009/0227876 A1 | 9/2009 | Tran |
| 2009/0233769 A1 | 9/2009 | Pryor |
| 2009/0233770 A1 | 9/2009 | Vincent et al. |
| 2009/0258710 A1 | 10/2009 | Quatrochi et al. |
| 2009/0269728 A1 | 10/2009 | Verstegen et al. |
| 2009/0298024 A1 | 12/2009 | Batzler et al. |
| 2009/0298650 A1 | 12/2009 | Kutliroff |
| 2009/0299232 A1 | 12/2009 | Lanfermann et al. |
| 2010/0016678 A1 | 1/2010 | Beck et al. |
| 2010/0036288 A1 | 2/2010 | Lanfermann et al. |
| 2010/0056340 A1 | 3/2010 | Ellis et al. |
| 2010/0063778 A1 | 3/2010 | Schrock et al. |
| 2010/0063779 A1 | 3/2010 | Schrock et al. |
| 2010/0069148 A1 | 3/2010 | Cargill |
| 2010/0088023 A1 | 4/2010 | Werner |
| 2010/0094174 A1 | 4/2010 | Choi et al. |
| 2010/0105531 A1 | 4/2010 | Crawford |
| 2010/0125026 A1 | 5/2010 | Zavadsky et al. |
| 2010/0125028 A1 | 5/2010 | Heppert |
| 2010/0137748 A1 | 6/2010 | Sone et al. |
| 2010/0144414 A1 | 6/2010 | Edis et al. |
| 2010/0197462 A1 | 8/2010 | Piane, Jr. |
| 2010/0204616 A1 | 8/2010 | Shears et al. |
| 2010/0205542 A1 | 8/2010 | Walman |
| 2010/0210359 A1 | 8/2010 | Krzeslo et al. |
| 2010/0210975 A1 | 8/2010 | Anthony, III et al. |
| 2010/0217738 A1 | 8/2010 | Sarel |
| 2010/0227302 A1 | 9/2010 | McGilvery et al. |
| 2010/0234184 A1 | 9/2010 | Le Page et al. |
| 2010/0248901 A1 | 9/2010 | Martens |
| 2010/0273610 A1 | 10/2010 | Johnson |
| 2010/0277411 A1 | 11/2010 | Yee et al. |
| 2010/0281432 A1 | 11/2010 | Geisner et al. |
| 2010/0302142 A1 | 12/2010 | French et al. |
| 2010/0306712 A1 | 12/2010 | Snook et al. |
| 2010/0316983 A1 | 12/2010 | Johns, Jr. |
| 2010/0332243 A1 | 12/2010 | Weigman et al. |
| 2011/0027135 A1 | 2/2011 | Michiaki et al. |
| 2011/0039659 A1 | 2/2011 | Kim et al. |
| 2011/0072457 A1 | 3/2011 | Lanfermann et al. |
| 2011/0077129 A1 | 3/2011 | Martens |
| 2011/0082397 A1 | 4/2011 | Alberts |
| 2011/0111922 A1 | 5/2011 | Weinman et al. |
| 2011/0111924 A1 | 5/2011 | Jones et al. |
| 2011/0112771 A1 | 5/2011 | French |
| 2011/0131005 A1 | 6/2011 | Ueshima et al. |
| 2011/0136627 A1 | 6/2011 | Williams |
| 2011/0158912 A1 | 6/2011 | Wright et al. |
| 2011/0212791 A1 | 9/2011 | Ueda et al. |
| 2011/0224557 A1 | 9/2011 | Banet et al. |
| 2011/0229864 A1 | 9/2011 | Short et al. |
| 2011/0251021 A1 | 10/2011 | Zavadsky et al. |
| 2011/0251495 A1 | 10/2011 | Province et al. |
| 2011/0270135 A1 | 11/2011 | Dooley et al. |
| 2011/0275907 A1 | 11/2011 | Inciardi et al. |
| 2011/0304497 A1 | 12/2011 | Molyneux et al. |
| 2011/0306491 A1 | 12/2011 | Belisle |
| 2011/0307821 A1 | 12/2011 | Martens |
| 2012/0034971 A1 | 2/2012 | Harp et al. |
| 2012/0038627 A1 | 2/2012 | Sung et al. |
| 2012/0041767 A1 | 2/2012 | Hoffman et al. |
| 2012/0052972 A1 | 3/2012 | Bentley |
| 2012/0077641 A1 | 3/2012 | Dyer et al. |
| 2012/0130515 A1 | 5/2012 | Homsi et al. |
| 2012/0130886 A1 | 5/2012 | Shergill et al. |
| 2012/0143064 A1 | 6/2012 | Cyphery et al. |
| 2012/0143358 A1 | 6/2012 | Adams et al. |
| 2012/0150074 A1 | 6/2012 | Yanev et al. |
| 2012/0165703 A1 | 6/2012 | Bottum et al. |
| 2012/0183939 A1 | 7/2012 | Aragones et al. |
| 2012/0183940 A1 | 7/2012 | Aragones et al. |
| 2012/0190505 A1 | 7/2012 | Shavit et al. |
| 2012/0234111 A1 | 9/2012 | Molyneux et al. |
| 2012/0253484 A1 | 10/2012 | Burich et al. |
| 2012/0254934 A1 | 10/2012 | McBrearty et al. |
| 2012/0268592 A1 | 10/2012 | Aragones et al. |
| 2012/0271143 A1 | 10/2012 | Aragones et al. |
| 2012/0274554 A1* | 11/2012 | Kinoshita ............ A61B 5/7445 345/156 |
| 2012/0277891 A1 | 11/2012 | Aragones et al. |
| 2012/0291544 A1* | 11/2012 | Kawabe ................ G01C 22/006 73/488 |
| 2012/0315986 A1 | 12/2012 | Walling |
| 2012/0315987 A1 | 12/2012 | Walling |
| 2013/0019694 A1 | 1/2013 | Molyneux et al. |
| 2013/0022947 A1 | 1/2013 | Muniz Simas et al. |
| 2013/0022950 A1 | 1/2013 | Muniz Simas et al. |
| 2013/0108993 A1 | 5/2013 | Katz |
| 2013/0171596 A1 | 7/2013 | French |
| 2013/0268205 A1 | 10/2013 | Aragones et al. |
| 2013/0281796 A1 | 10/2013 | Pan |
| 2013/0295539 A1 | 11/2013 | Wilson et al. |
| 2013/0324368 A1 | 12/2013 | Aragones et al. |
| 2013/0325396 A1 | 12/2013 | Yuen et al. |
| 2013/0338802 A1 | 12/2013 | Winsper et al. |
| 2014/0073486 A1 | 3/2014 | Ahmed et al. |
| 2014/0278218 A1 | 9/2014 | Chang |
| 2014/0287388 A1 | 9/2014 | Ferrier |
| 2014/0308640 A1 | 10/2014 | Forman et al. |
| 2015/0105881 A1 | 4/2015 | Guerrero et al. |
| 2016/0199693 A1 | 7/2016 | Vermilyea et al. |

FOREIGN PATENT DOCUMENTS

| | | |
|---|---|---|
| CN | 1457246 A | 11/2003 |
| CN | 1457546 A | 11/2003 |
| CN | 1723847 A | 1/2006 |
| CN | 2803449 Y | 8/2006 |
| CN | 1933880 A | 3/2007 |
| CN | 101061949 A | 10/2007 |
| CN | 101202994 A | 6/2008 |
| CN | 101330863 A | 12/2008 |

(56) References Cited

FOREIGN PATENT DOCUMENTS

| | | | |
|---|---|---|---|
| CN | 201242749 Y | 5/2009 | |
| CN | 101558996 A | 10/2009 | |
| CN | 101668482 A | 3/2010 | |
| CN | 201643611 U | 11/2010 | |
| CN | 101909705 A | 12/2010 | |
| CN | 101910846 A | 12/2010 | |
| CN | 101964047 A | 2/2011 | |
| CN | 101978374 A | 2/2011 | |
| CN | 102068264 A | 5/2011 | |
| CN | 102089041 A | 6/2011 | |
| CN | 103154954 A | 6/2013 | |
| CN | 103493056 A | 1/2014 | |
| DE | 29720110 U1 | 1/1998 | |
| EP | 0956819 A1 | 11/1999 | |
| EP | 2324762 A1 * | 5/2011 | ........... A61B 5/0205 |
| GB | 2415788 A | 1/2006 | |
| JP | H8-57093 A | 3/1996 | |
| JP | 857093 | 5/1996 | |
| JP | H08251577 A | 9/1996 | |
| JP | H0938051 A | 2/1997 | |
| JP | H10502465 A | 3/1998 | |
| JP | 2000033184 A | 2/2000 | |
| JP | 2000070242 A | 3/2000 | |
| JP | 2000504854 A | 4/2000 | |
| JP | 2001224853 A | 8/2001 | |
| JP | 2001231904 A | 8/2001 | |
| JP | 2001299975 A | 10/2001 | |
| JP | 2002112984 A | 4/2002 | |
| JP | 2002516121 A | 6/2002 | |
| JP | 2002253718 A | 9/2002 | |
| JP | 2002291952 A | 10/2002 | |
| JP | 2003085288 A | 3/2003 | |
| JP | 2003141260 A | 5/2003 | |
| JP | 2003290406 A | 10/2003 | |
| JP | 2004054393 A | 2/2004 | |
| JP | 2004073272 A | 3/2004 | |
| JP | 2004089727 A | 3/2004 | |
| JP | 2004097649 A | 4/2004 | |
| JP | 2004208995 A | 7/2004 | |
| JP | 2005034195 A | 2/2005 | |
| JP | 3656853 B2 | 6/2005 | |
| JP | 2005198818 A | 7/2005 | |
| JP | 2005230068 A | 9/2005 | |
| JP | 2006130127 A | 5/2006 | |
| JP | 2006167313 A | 6/2006 | |
| JP | 2006263002 A | 10/2006 | |
| JP | 2006302122 A | 11/2006 | |
| JP | 2006320424 A | 11/2006 | |
| JP | 2007143748 A | 6/2007 | |
| JP | 2007144107 A | 6/2007 | |
| JP | 2007260307 A | 10/2007 | |
| JP | 2008104758 A | 5/2008 | |
| JP | 2008295746 A | 12/2008 | |
| JP | 2009048757 A | 3/2009 | |
| JP | 2009050699 A | 3/2009 | |
| JP | 2009078134 A | 4/2009 | |
| JP | 2009172315 A | 8/2009 | |
| JP | 2009201672 A | 9/2009 | |
| JP | 2009213656 A | 9/2009 | |
| JP | 2009213782 A | 9/2009 | |
| JP | 2009219828 A | 10/2009 | |
| JP | 2009247836 A | 10/2009 | |
| JP | 2009279041 A | 12/2009 | |
| JP | 2010502368 A | 1/2010 | |
| JP | 2010069102 A | 4/2010 | |
| JP | 2010075715 A | 4/2010 | |
| JP | 2010086358 A | 4/2010 | |
| JP | 2010188159 A | 9/2010 | |
| JP | 2010246636 A | 11/2010 | |
| JP | 2010259456 A | 11/2010 | |
| JP | 2011152333 A | 8/2011 | |
| KR | 20030041034 A | 5/2003 | |
| KR | 20090084035 A | 8/2009 | |
| KR | 20100086052 A | 7/2010 | |
| TW | 200639682 A | 11/2006 | |
| TW | 200825989 A | 6/2008 | |
| TW | 200915213 A | 4/2009 | |
| TW | 200950748 A | 12/2009 | |
| WO | 9729814 A1 | 8/1997 | |
| WO | 2001045014 A1 | 6/2001 | |
| WO | 2002035997 A1 | 5/2002 | |
| WO | 2002055959 A1 | 7/2002 | |
| WO | 2002067449 A2 | 8/2002 | |
| WO | 2002101408 A1 | 12/2002 | |
| WO | 2004073494 A2 | 9/2004 | |
| WO | 2005018759 A1 | 3/2005 | |
| WO | 2006098282 A1 | 9/2006 | |
| WO | WO-2006111687 A1 * | 10/2006 | ............... A61B 5/22 |
| WO | 2008060043 A1 | 5/2008 | |
| WO | 2009043024 A1 | 4/2009 | |
| WO | 2009073607 A2 | 6/2009 | |
| WO | 2010121166 A1 | 10/2010 | |
| WO | 2012021633 A2 | 2/2012 | |
| WO | 2012039467 A1 | 3/2012 | |
| WO | 2012061438 A2 | 5/2012 | |
| WO | 2012061804 A1 | 5/2012 | |
| WO | 2012071548 A1 | 5/2012 | |
| WO | 2012071551 A1 | 5/2012 | |

OTHER PUBLICATIONS

Jun. 27, 2013 (WO)—International Preliminary Report on Patentability—App. No. PCT/US2011/064711.
May 31, 2013 (WO)—International Search Report and Written Opinion—App. No. PCT/US2012/066070.
May 29, 2013 (WO)—International Search Report and Written Opinion—App. No. PCT/US2012/066065.
Jun. 6, 2013 (WO)—International Preliminary Report on Patentability—App. No. PCT/US20111062117.
May 16, 2013 (WO)—International Preliminary Report on Patentability—App. No. PCT/US20111059559.
Apr. 3, 2012—(WO) ISR &WO—App. No. PCT/US11/1064711.
Feb. 23, 2012—(WO) ISR & WO—App. No. PCT/US2011/062117.
Feb. 20, 2014 (WO)—International Search Report and Written Opinion—App. No. PCT/US2013/067512.
Sep. 12, 2013—(WO) ISR & WO—App. No. PCT/US2013/044109.
Zhao, et al., Design and Practice for Individual Specialized PC Expert System for College Student, Journal of Xi An Institute of Physical Education, vol. 22, No. 2 (Mar. 2005) pp. 118-121.
Plagge et al: "Design and Evaluation of the T-Team of the University of Tuebingen for RoboCup '98" in "Network and Parallel Computing", Jan. 1, 1999 (Jan. 1, 1999), Springer Inernational Publishing, Cham 032548, XP055334016, ISSN: 0302-9743, ISBN: 978-3-642-23677-8, vol. 1604, pp. 464-472, DOI: 40.1007/3-540-48422-1_47.
Translation of JP2009201672A, Published Sep. 10, 2009 [Retrieved Oct. 11, 2017] Retrieved from Google Patents <URL:https://patents.google.com/patent/JP2009201672A/en>.
Autotranslation of JP2009-201672, published Sep. 10, 2009 [Retrieved Oct. 13, 2017] Retrieved from JPO using AIPN system.
Jul. 26, 2022 (EP)—Extended European Search Report—App. No. 22169770.9.
United States District Court Southern District of New York (Foley Square), "Complaint (w/o exhibits)", NIKE, Inc. v. Lululemon Athletica Inc. et al., Case 1:22-cv-00082, filed Jan. 5, 2022, 29 pages.
United States District Court Southern District of New York (Foley Square), "Answer", NIKE, Inc. v. Lululemon Athletica Inc. et al., Case 1:22-cv-00082, filed Jan. 14, 2022, 15 pages.
United States District Court Southern District of New York (Foley Square), "Docket", NIKE, Inc. v. Lululemon Athletica Inc. et al., Case 1:22-cv-00082, printed Jul. 26, 2022, 8 pages.
United States District Court Southern District of New York (Foley Square), Defendant's "Disclosure of Preliminary Invalidity Contentions", NIKE, Inc. v. Lululemon Athletica Inc. et al., Case 1:22-cv-00082, filed Jul. 18, 2022, 1097 pages.
United States District Court Southern District of New York (Foley Square), Defendant's "Amended Exhibits", (Exhs. D-1, E-1, E-2,

(56) References Cited

OTHER PUBLICATIONS

E-3, E-4, E-5, E-6) *NIKE, Inc. v. Lululemon Athletica Inc. et al.,* Case 1:22-cv-00082, filed Jul. 26, 2022, 183 pages.
David R. Bassett, Jr., Validity and Reliability Issues in Objective Monitoring of Physical Activity, Research Quarterly for Exercise and Sport, vol. 71, No. 2, pp. 30-36 (2000) ("Bassett"), 7 pages.
Chris Hall, Nokia Sports Tracker, Pocket-lint (Jul. 25, 2008), https://www.pocket-lint.com/phones/reviews/nokia/70414-nokia-sports-tracker-mobile-application ("Hall"), 11 pages.
Jozsef Hajdu, Provided Services of Social Networks for Sport, TKK T-110.5190 Seminar on Internetworking (Apr. 28-29, 2008), http://www.cse.tkk.fi/en/publications/B/1/papers/Hajdu_final.pdf ("Hajdu"), 8 pages.
Zee, Breaking: Goodbye Twitter? Facebook adds @mentions to status updates (Sep. 10, 2009, 9:16 PM), https://thenextweb.com/news/breaking-facebook-adds-mentions-status-updates?amp=1 ("Zee"), 6 pages.
Robert Anderson (@rsa), Twitter (Nov. 2, 2006, 11:58 PM), https://twitter.com/rsa/status/55281?lang=en ("Anderson"), 3 pages.
Scott Tousignant (@TheFitB), Twitter (Nov. 27, 2008, 12:27 PM), https://twitter.com/TheFitB/status/1026679285 ("Tousignant"), 1 page.
Internet webpage wii.nintendo.com/controller.jsp, dated Nov. 30, 2006 and retrieved from the Internet Archive ("Nintendo webpage").
U.S. Appl. No. 17/737,843, filed May 5, 2022, Teresa Aragones et al.
U.S. Appl. No. 17/737,870, filed May 5, 2022, Teresa Aragones et al.
U.S. Appl. No. 14/943,961, filed Nov. 17, 2015, Tesa Aragones et al.
U.S. Appl. No. 15/609,084, filed May 31, 2017, Tesa Aragones et al.
U.S. Appl. No. 17/031,300, filed Sep. 24, 2020, Teresa Aragones et al.
U.S. Appl. No. 17/387,656, filed Jul. 28, 2021, Teresa Aragones et al.
Jan. 4, 2023—Petition (w/Exh. 1001 (U.S. Pat. No. 10,188,930)) for Inter Partes Review of U.S. Pat. No. 10,188,930, Case No. IPR2023-00348, U.S. Patent Office, Before the Patent Trial and Appeal Board, 110 pages.
Declaration and Curriculum Vitae of Dr. Gregory S. Fischer, Jan. 4, 2023, 148 pages (Ex. 1005, IPR Pet.).
Aug. 14, 2017—Application as filed, U.S. Appl. No. 15/675,895 (Ex. 1006, IPR Pet.).
Jun. 19, 2018—Non-Final Rejection, U.S. Appl. No. 15/675,895 (Ex. 1007, IPR Pet.).
Sep. 13, 2018—Response to Non-Final Office Action and Terminal Disclaimer filed, U.S. Appl. No. 15/675,895 (Ex. 1008, IPR Pet.).
Oct. 30, 2018—Notice of Allowance, U.S. Appl. No. 15/675,895 (Ex. 1009, IPR Pet.).
Jan. 9, 2019—Issue Notification, U.S. Appl. No. 15/675,895 (Ex. 1010, IPR Pet.).
Motorola DROID PRO XT610 Description, 2 pages (Ex. 1011, IPR Pet.).
Lara Allet et al, Wearable Systems for Monitoring Mobility-Related Activities in Chronic Disease: A Systematic Review, Sensors 2010, 27 pages (Ex. 1012, IPR Pet.).
Praveen Kumar Diwakar et al, Personal Digital Exercise Trainer for Managing, Monitoring and Recording the Exercise, IEEE, Sep. 1-4, 2005, 4 pages (Ex. 1013, IPR Pet.).
Nike + iPod web page, Internet Archive waybackmachine, https://www.apple.com/ipod/nike/; 1 page (Ex. 1014, IPR Pet.).
Nike + iPod manual, 2009, 28 pages (Ex. 1015, IPR Pet.).
Gregory S. Sawicki et al, Mechanics and Energetics of Level Walking with Powered Ankle Exoskeletons, Journal of Experimental, 12 pages (Ex. 1016, IPR Pet.).
Machine Translation of Zhao Jiang hong, Liu Zhi Qiar, Shi Bin. Design and Practice for Individual Specialized PC Expert System for College Student. Journal of Xi'An Institute of Physical Education, vol. 22 No. 2 Mar. 2005 (16 pages) <retrieved from Google Translate on Jun. 29, 2016>.
Jun. 25, 2024—Judgment, Final Written Decision, IPR2023-00348, U.S. Pat. No. 10,188,930 B2, Paper 34, 62 pages.

\* cited by examiner

USER INTERFACE FOR REMOTE JOINT WORKOUT SESSION

CROSS-REFERENCE TO RELATED APPLICATIONS

This application is a continuation of U.S. patent application Ser. No. 17/031,300, filed Sep. 24, 2020, which is a continuation of U.S. patent application Ser. No. 15/857,320, filed Dec. 28, 2017, which is a continuation of U.S. patent application Ser. No. 13/664,251, filed Oct. 30, 2012, now U.S. Pat. No. 9,977,874, which is a continuation-in-part of U.S. patent application Ser. No. 13/324,812, filed Dec. 13, 2011, now U.S. Pat. No. 9,852,271; and a continuation-in-part application of U.S. patent application Ser. No. 13/304,056, filed Nov. 23, 2011, now U.S. Pat. No. 9,223,936; and a continuation-in-part application of U.S. patent application Ser. No. 13/290,478, filed Nov. 7, 2011, now U.S. Pat. No. 9,358,426; and a continuation-in-part of U.S. patent application Ser. No. 13/290,359, filed Nov. 7, 2011, now U.S. Pat. No. 9,283,429; and a continuation-in-part application of U.S. patent application Ser. No. 13/304,064, filed Nov. 23, 2011, now U.S. Pat. No. 9,457,256. This application also claims the benefit of, and priority to U.S. Provisional Patent Application Ser. No. 61/655,365 filed Jun. 4, 2012. The contents of each of the above-identified applications are expressly incorporated herein by reference in their entireties for any and all non-limiting purposes.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this clear separation between athletic activity and other activities reduces the amount of motivation that an individual might have toward exercising. Further, athletic activity services and systems directed toward encouraging individuals to engage in athletic activities might also be too focused on one or more particular activities while an individual's interest are ignored. This may further decrease a user's interest in participating in athletic activities or using the athletic activity services and systems.

Therefore, improved systems and methods to address these and other shortcomings in the art are desired.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of this disclosure relate to processing of data taken while a user performs an athletic activity to determine an estimate of energy expenditure such as, for example, an amount of calories burned.

Example embodiments may relate to a system, method, apparatus, and computer readable media configured for prompting a user to perform an exercise and calculating an energy expenditure estimate for the user performing the exercise. This may be based on a type of the exercise and/or on the form of the user. In other embodiments, expenditure estimate may be, or comprise, for example, an estimate of calories burned by the user. In certain embodiments, energy expenditure calculations comprise determinations relating to: effort, oxygen consumed, and/or oxygen kinetics of the user.

Certain aspects of this disclosure relate to a graphical user interface (UI) configured to facilitate a joint session of two or more remote users. Despite being at different physical locations, users may still compete and/or collectively engage in athletic activities. In one embodiment, each of a plurality of users may engage in a competition in substantially real-time. Thus, aspects of this disclosure relate to system and methods that may simultaneously present a UI on two remote display devices in which the users may conduct a joint session despite being remotely located. Virtual trainer renditions may be configured to simultaneously prompt the remote users to perform a specific exercise. For example, one or more devices may cause the respective displays to present a virtual trainer rendition demonstrating an exercise to instruct the users.

Further aspects of this disclosure relate to generating and updating a UI based upon real-time fitness or movement data obtained from two or more users that are located at different locations. In certain embodiments, the local UI rendition may only show the graphical representation of the local user inclusive of any adjustments based upon the user's real-time movements and not other graphical representations of other remote users. Certain embodiments may be configured to simultaneous display real-time image data of a plurality of users associated with the joint session on a single display device.

Calculated energy expenditure determinations based upon the respective users' real-time performances may be simultaneously displayed on a user interface. In certain embodiments, interface renditions may be updated in real-time to reflect values (such as an energy expenditure value) associated with the respective movements of users responsive to the instructions provided by virtual one or more trainers. Thus, according to certain implementations, a plurality of users may readily view not only which user has the highest value, or the energy expended per unit time, but also determine how close the other user's value is to theirs, whether the other user(s) are getting closer or further, and/or determinations relating to other users performances on specific routines. Still yet further embodiments, an interface may be configured to display a joint total of points determined from the joint movements of at least two users.

Further aspects of this disclosure relate to selecting and displaying a meter on a user interface. In certain embodiments, a meter may be selected from a plurality of meters. The selected meter for an attribute of a first user's performance may be simultaneous displayed on multiple renditions of UI.

The meter(s) may be updated in real-time as the users perform the predetermined athletic activity. Thus in certain embodiments, each of a plurality of users remotely located from at least one other user may compare their performance with at least one other user. The updating of the meter(s) may be based upon sensor data, such as described herein. In one embodiment, the properties of at least the first selected meter may be based upon data received from the at least one sensor located at the first location and simultaneously altering the properties of the second selected meter based upon data received from the at least one sensor at the second location.

These and other aspects of the embodiments are discussed in greater detail throughout this disclosure, including the accompanying drawings.

BRIEF DESCRIPTION OF THE DRAWINGS

The present disclosure is illustrated by way of example and not limited in the accompanying figures in which like reference numerals indicate similar elements and in which:

FIGS. 1A-C illustrate an example of a system for providing personal training in accordance with example embodiments, wherein FIG. 1A illustrates an example network configured to monitor athletic activity, FIG. 1B illustrates an example computing device in accordance with example embodiments, and FIG. 1C illustrates example sensory locations that may be utilized for monitoring user performance during physical activity in accordance with example embodiments;

FIGS. 4A-B illustrate an example user interface that may be implemented in accordance with example embodiments, wherein FIG. 4A shows a first rendition of the user interface and FIG. 4B shows a second rendition of the interface which may be simultaneously displayed to a remote user in a remote location;

FIG. 8A shows an example cardio meter 802 and FIG. 8B shows an example strength meter 804.

DETAILED DESCRIPTION

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

I. Example Personal Training System

A. Illustrative Computing Devices

Figure 1A:
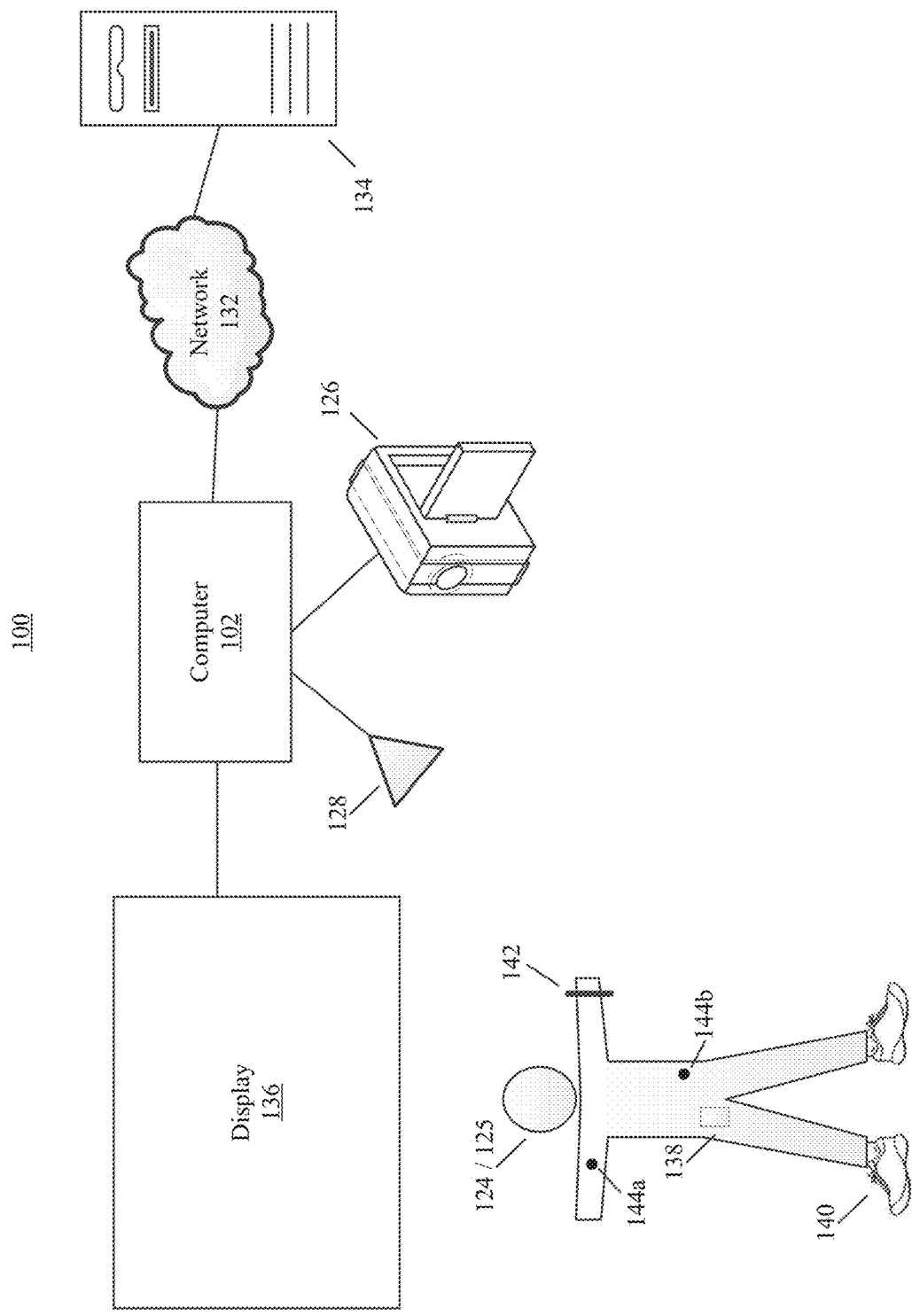

FIG. 1A illustrates an example of a personal training system 100 in accordance with example embodiments. Example system 100 may include one or more electronic devices, such as computer 102. Computer 102 may comprise a mobile terminal, such as a telephone, music player, tablet, netbook or any portable device. In other embodiments, computer 102 may comprise a set-top box (STB), desktop computer, digital video recorder(s) (DVR), computer server(s), and/or any other desired computing device. In certain configurations, computer 102 may comprise a gaming console, such as for example, a Microsoft® XBOX, Sony® Playstation, and/or a Nintendo® Wii gaming consoles. Those skilled in the art will appreciate that these are merely example consoles for descriptive purposes and this disclosure is not limited to any console or device.

Figure 1B:
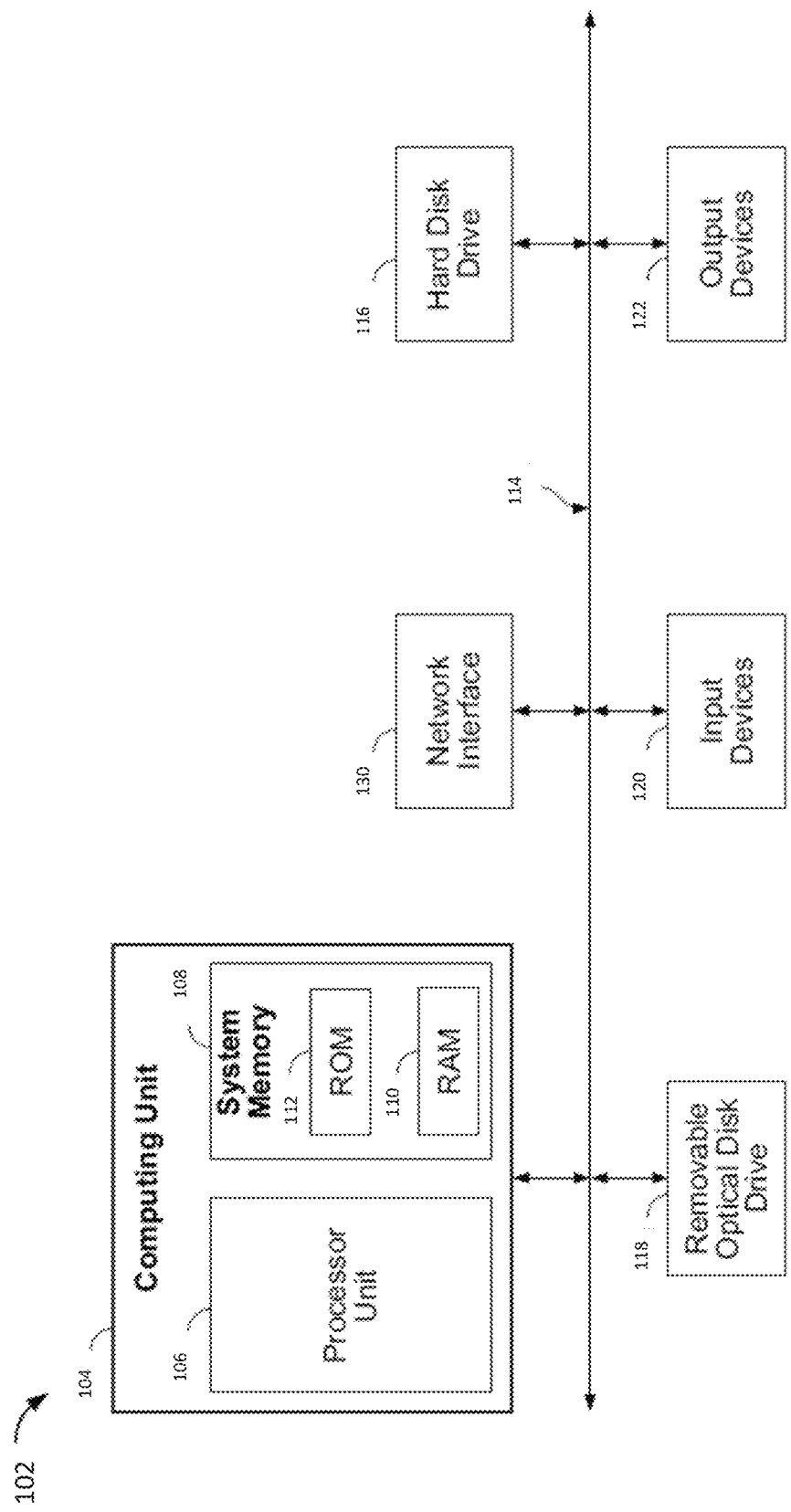

Turning briefly to FIG. 1B, computer 102 may include computing unit 104, which may comprise at least one processing unit 106. Processing unit 106 may be any type of processing device for executing software instructions, such as for example, a microprocessor device. Computer 102 may include a variety of non-transitory computer readable media, such as memory 108. Memory 108 may include, but is not limited to, random access memory (RAM) such as RAM 110, and/or read only memory (ROM), such as ROM 112. Memory 108 may include any of: electronically erasable programmable read only memory (EEPROM), flash memory or other memory technology, CD-ROM, digital versatile disks (DVD) or other optical disk storage, magnetic storage devices, or any other medium that can be used to store the desired information and that can be accessed by computer 102.

The processing unit 106 and the system memory 108 may be connected, either directly or indirectly, through a bus 114 or alternate communication structure to one or more peripheral devices. For example, the processing unit 106 or the system memory 108 may be directly or indirectly connected to additional memory storage, such as a hard disk drive 116, a removable magnetic disk drive, an optical disk drive 118, and a flash memory card. The processing unit 106 and the system memory 108 also may be directly or indirectly connected to one or more input devices 120 and one or more output devices 122. The output devices 122 may include, for example, a display device 136, television, printer, stereo, or speakers. In some embodiments one or more display devices may be incorporated into eyewear. The display devices incorporated into eyewear may provide feedback to users. Eyewear incorporating one or more display devices also provides for a portable display system. The input devices 120 may include, for example, a keyboard, touch screen, a remote control pad, a pointing device (such as a mouse, touchpad, stylus, trackball, or joystick), a scanner, a camera or a microphone. In this regard, input devices 120 may comprise one or more sensors configured to sense, detect, and/or measure athletic movement from a user, such as user(s) 124/125, shown in FIG. 1A. As used herein, an "athletic movement" includes movements relating to fitness, exercise, flexibility, including movements that may be part of one or more single and multiple participant athletic competitions, exercise routines, and/or combinations thereof. Further although one user is shown to represent multiple users (e.g., 124/125), those skilled in the art will appreciate that user 124 and 125 are not required to, but may, have one or more of the same types of sensors. Further, one or more users 124/125 may be located at remote locations from each other.

Looking again to FIG. 1A, image-capturing device 126 and/or sensor 128 may be utilized in detecting and/or measuring athletic movements of user 124. In one embodiment, data obtained from image-capturing device 126 or sensor 128 may directly detect athletic movements, such that the data obtained from image-capturing device 126 or sensor 128 is directly correlated to a motion parameter. For example, and with reference to FIG. 4, image data from image-capturing device 126 may detect that the distance between sensor locations 402g and 402i has decreased and therefore, image-capturing device 126 alone may be configured to detect that user's 124 right arm has moved. Yet, in other embodiments, data from image-capturing device 126 and/or sensor 128 may be utilized in combination, either with each other or with other sensors to detect and/or measure movements. Thus, certain measurements may be determined from combining data obtained from two or more devices. Image-capturing device 126 and/or sensor 128 may include or be operatively connected to one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Example uses of illustrative sensors 126, 128 are provided below in Section I.C, entitled "Illustrative Sensors." Computer 102 may also use touch screens or image capturing device to determine where a user is pointing to make selections from a graphical user interface. One or more embodiments may utilize one or more wired and/or wireless technologies, alone or in combination, wherein examples of wireless technologies include Bluetooth® technologies, Bluetooth® low energy technologies, and/or ANT technologies.

B. Illustrative Network

Still further, computer 102, computing unit 104, and/or any other electronic devices may be directly or indirectly connected to one or more network interfaces, such as example interface 130 (shown in FIG. 1B) for communicating with a network, such as network 132. In the example of FIG. 1B, network interface 130, may comprise a network adapter or network interface card (NIC) configured to translate data and control signals from the computing unit 104 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 130 may employ any suitable connection agent for connecting to a network, including, for example, a wireless transceiver, a power line adapter, a modem, or an Ethernet connection. Network 132, however, may be any one or more information distribution network(s), of any type(s) or topology(s), alone or in combination(s), such as internet(s), intranet(s), cloud(s), LAN(s). Network 132 may be any one or more of cable, fiber, satellite, telephone, cellular, wireless, etc. Networks are well known in the art, and thus will not be discussed here in more detail. Network 132 may be variously configured such as having one or more wired or wireless communication channels to connect one or more locations (e.g., schools, businesses, homes, consumer dwellings, network resources, etc.), to one or more remote servers 134, or to other computers, such as similar or identical to computer 102. Indeed, system 100 may include more than one instance of each component (e.g., more than one computer 102, more than one display 136, etc.).

Regardless of whether computer 102 or other electronic device within network 132 is portable or at a fixed location, it should be appreciated that, in addition to the input, output and storage peripheral devices specifically listed above, the computing device may be connected, such as either directly, or through network 132 to a variety of other peripheral devices, including some that may perform input, output and storage functions, or some combination thereof. In certain embodiments, a single device may integrate one or more components shown in FIG. 1A. For example, a single device may include computer 102, image-capturing device 126, sensor 128, display 136 and/or additional components. In one embodiment, sensor device 138 may comprise a mobile terminal having a display 136, image-capturing device 126, and one or more sensors 128. Yet, in another embodiment, image-capturing device 126, and/or sensor 128 may be peripherals configured to be operatively connected to a media device, including for example, a gaming or media system. Thus, it goes from the foregoing that this disclosure is not limited to stationary systems and methods. Rather, certain embodiments may be carried out by a user 124 in almost any location.

A. Illustrative Sensors

Computer 102 and/or other devices may comprise one or more sensors 126, 128 configured to detect and/or monitor at least one fitness parameter of a user 124. Sensors 126 and/or 128 may include, but are not limited to: an accelerometer, a gyroscope, a location-determining device (e.g., GPS), light sensor, temperature sensor (including ambient temperature and/or body temperature), sleep pattern sensors, heart rate monitor, image-capturing sensor, moisture sensor and/or combinations thereof. Network 132 and/or computer 102 may be in communication with one or more electronic devices of system 100, including for example, display 136, an image capturing device 126 (e.g., one or more video cameras), and sensor 128, which may be an infrared (IR) device. In one embodiment sensor 128 may comprise an IR transceiver. For example, sensors 126, and/or 128 may transmit waveforms into the environment, including towards the direction of user 124 and receive a "reflection" or otherwise detect alterations of those released waveforms. In yet another embodiment, image-capturing device 126 and/or sensor 128 may be configured to transmit and/or receive other wireless signals, such as radar, sonar, and/or audible information. Those skilled in the art will readily appreciate that signals corresponding to a multitude of different data spectrums may be utilized in accordance with various embodiments. In this regard, sensors 126 and/or 128 may detect waveforms emitted from external sources (e.g., not system 100). For example, sensors 126 and/or 128 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology. As a non-limited example, image-capturing devices configured to perform range phenomenology are commercially available from Flir Systems, Inc. of Portland, Oregon Although image capturing device 126 and sensor 128 and display 136 are shown in direct (wirelessly or wired) communication with computer 102, those skilled in the art will appreciate that any may directly communicate (wirelessly or wired) with network 132.

Multi-Purpose Electronic Devices

User 124 may possess, carry, and/or wear any number of electronic devices, including sensory devices 138, 140, 142, and/or 144. In certain embodiments, one or more devices 138, 140, 142, 144 may not be specially manufactured for fitness or athletic purposes. Indeed, aspects of this disclosure relate to utilizing data from a plurality of devices, some of which are not fitness devices, to collect, detect, and/or measure athletic data. In one embodiment, device 138 may comprise a portable electronic device, such as a telephone or digital music player, including an IPOD®, IPAD®, or iPhone®, brand devices available from Apple, Inc. of Cupertino, California or Zune® or Microsoft® Windows devices available from Microsoft of Redmond, Washington As known in the art, digital media players can serve as both an output device for a computer (e.g., outputting music from a sound file or pictures from an image file) and a storage device. In one embodiment, device 138 may be computer 102, yet in other embodiments, computer 102 may be entirely distinct from device 138. Regardless of whether device 138 is configured to provide certain output, it may serve as an input device for receiving sensory information. Devices 138, 140, 142, and/or 144 may include one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. In certain embodiments, sensors may be passive, such as reflective materials that may be detected by image-capturing device 126 and/or sensor 128 (among others). In certain embodiments, sensors 144 may be integrated into apparel, such as athletic clothing. For instance, the user 124 may wear one or more on-body sensors 144a-b. Sensors 144 may be incorporated into the clothing of user 124 and/or placed at any desired location of the body of user 124. Sensors 144 may communicate (e.g., wirelessly) with computer 102, sensors 128, 138, 140, and 142, and/or camera 126. Examples of interactive gaming apparel are described in U.S. patent application Ser. No. 10/286,396, filed Oct. 30, 2002, and published as U.S. Pat. Pub, No. 2004/0087366, the contents of which are incorporated herein by reference in its entirety for any and all non-limiting purposes. In certain embodiments, passive sensing surfaces may reflect waveforms, such as infrared light, emitted by image-capturing device 126 and/or sensor 128. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Devices 138-144 may communicate with each other, either directly or through a network, such as network 132. Communication between one or more of devices 138-144 may communicate through computer 102. For example, two or more of devices 138-144 may be peripherals operatively connected to bus 114 of computer 102. In yet another embodiment, a first device, such as device 138 may communicate with a first computer, such as computer 102 as well as another device, such as device 142, however, device 142 may not be configured to connect to computer 102 but may communicate with device 138. Those skilled in the art will appreciate that other configurations are possible.

Some implementations of the example embodiments may alternately or additionally employ computing devices that are intended to be capable of a wide variety of functions, such as a desktop or laptop personal computer. These computing devices may have any combination of peripheral devices or additional components as desired. Also, the components shown in FIG. 1B may be included in the server 134, other computers, apparatuses, etc.

2. Illustrative Apparel/Accessory Sensors

In certain embodiments, sensory devices 138, 140, 142 and/or 144 may be formed within or otherwise associated with user's 124 clothing or accessories, including a watch, armband, wristband, necklace, shirt, shoe, or the like. Examples of shoe-mounted and wrist-worn devices (devices 140 and 142, respectively) are described immediately below, however, these are merely example embodiments and this disclosure should not be limited to such.

1. Shoe-Mounted Device

Figure 2:
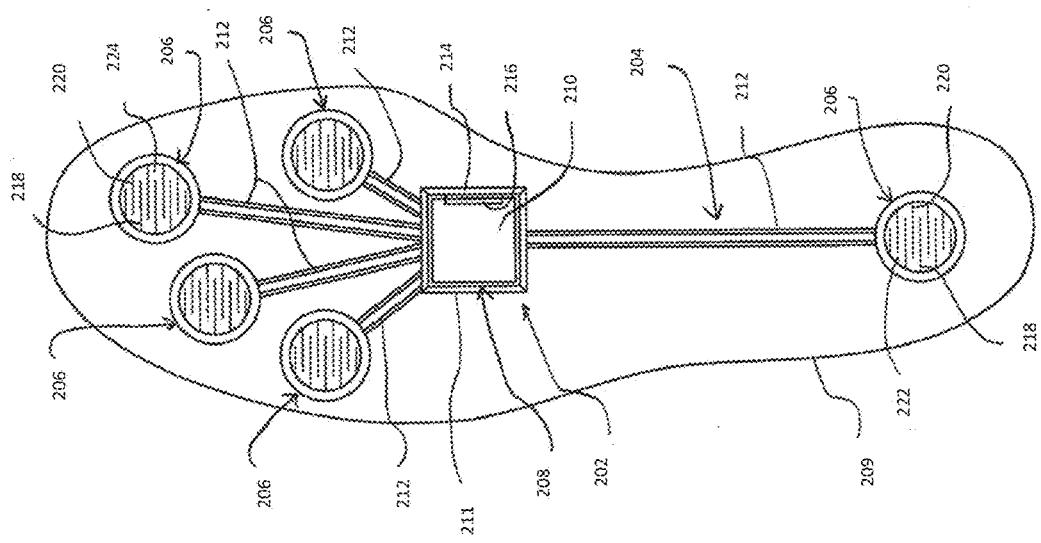
FIG. 2 illustrates an example sensor assembly that may be worn by a user in accordance with example embodiments.

In certain embodiments, sensory device 140 may comprise footwear which may include one or more sensors, including but not limited to: an accelerometer, location-sensing components, such as GPS, and/or a force sensor system. FIG. 2 illustrates one example embodiment of a sensor system 202. In certain embodiments, system 202 may include a sensor assembly 204. Assembly 204 may comprise one or more sensors, such as for example, an accelerometer, location-determining components, and/or force sensors. In the illustrated embodiment, assembly 204 incorporates a plurality of sensors, which may include force-sensitive resistor (FSR) sensors 206. In yet other embodiments, other sensor(s) may be utilized. Port 208 may be positioned within a sole structure 209 of a shoe. Port 208 may optionally be provided to be in communication with an electronic module 210 (which may be in a housing 211) and a plurality of leads 212 connecting the FSR sensors 206 to the port 208. Module 210 may be contained within a well or cavity in a sole structure of a shoe. The port 208 and the module 210 include complementary interfaces 214, 216 for connection and communication.

In certain embodiments, at least one force-sensitive resistor 206 shown in FIG. 2 may contain first and second electrodes or electrical contacts 218, 220 and a force-sensitive resistive material 222 disposed between the electrodes 218, 220 to electrically connect the electrodes 218, 220 together. When pressure is applied to the force-sensitive material 222, the resistivity and/or conductivity of the force-sensitive material 222 changes, which changes the electrical potential between the electrodes 218, 220. The change in resistance can be detected by the sensor system 202 to detect the force applied on the sensor 216. The force-sensitive resistive material 222 may change its resistance under pressure in a variety of ways. For example, the force-sensitive material 222 may have an internal resistance that decreases when the material is compressed, similar to the quantum tunneling composites described in greater detail below. Further compression of this material may further decrease the resistance, allowing quantitative measurements, as well as binary (on/off) measurements. In some circumstances, this type of force-sensitive resistive behavior may be described as "volume-based resistance," and materials exhibiting this behavior may be referred to as "smart materials." As another example, the material 222 may change the resistance by changing the degree of surface-to-surface contact. This can be achieved in several ways, such as by using microprojections on the surface that raise the surface resistance in an uncompressed condition, where the surface resistance decreases when the microprojections are compressed, or by using a flexible electrode that can be deformed to create increased surface-to-surface contact with another electrode. This surface resistance may be the resistance between the material 222 and the electrode 218, 220 222 and/or the surface resistance between a conducting layer (e.g., carbon/graphite) and a force-sensitive layer (e.g., a semiconductor) of a multi-layer material 222. The greater the compression, the greater the surface-to-surface contact, resulting in lower resistance and enabling quantitative measurement. In some circumstances, this type of force-sensitive resistive behavior may be described as "contact-based resistance." It is understood that the force-sensitive resistive material 222, as defined herein, may be or include a doped or non-doped semiconducting material.

The electrodes 218, 220 of the FSR sensor 216 can be formed of any conductive material, including metals, carbon/graphite fibers or composites, other conductive composites, conductive polymers or polymers containing a conductive material, conductive ceramics, doped semiconductors, or any other conductive material. The leads 212 can be connected to the electrodes 218, 220 by any suitable method, including welding, soldering, brazing, adhesively joining, fasteners, or any other integral or non-integral joining method. Alternately, the electrode 218, 220 and associated lead 212 may be formed of a single piece of the same material.

ii. Wrist-Worn Device

Figure 3:
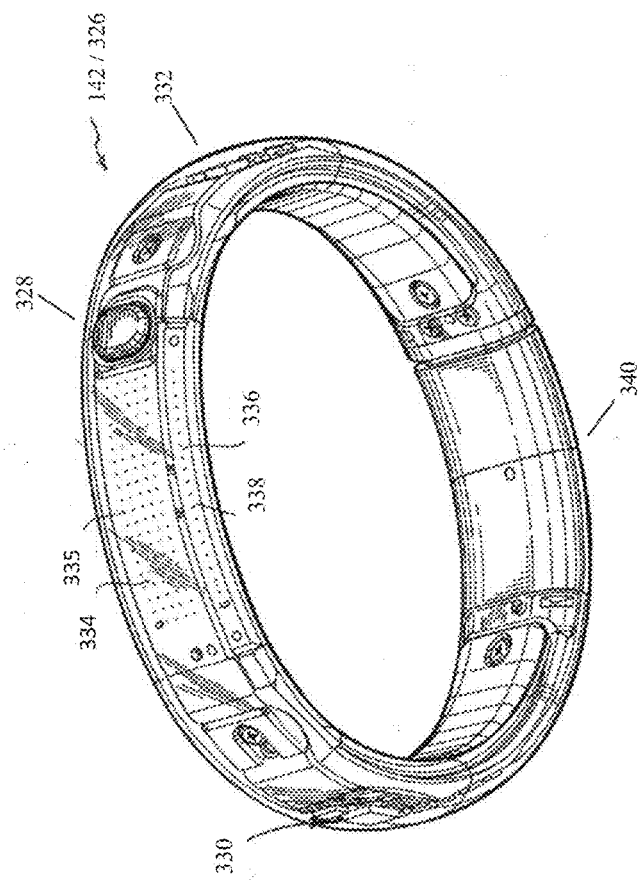
FIG. 3 illustrates another example sensor assembly that may be worn by a user in accordance with example embodiments.

As shown in FIG. 3, device 326 (which may resemble or be sensory device 142 shown in FIG. 1A) may be configured to be worn by user 124, such as around a wrist, arm, ankle or the like. Device 326 may monitor athletic movements of a user, including all-day activity of user 124. In this regard, device 326 may detect athletic movement during user's 124 interactions with computer 102 and/or operate independently of computer 102. For example, in one embodiment, device 326 may be an-all day activity monitor that measures activity regardless of the user's proximity or interactions with computer 102. Device 326 may communicate directly with network 132 and/or other devices, such as devices 138 and/or 140. In other embodiments, athletic data obtained from device 326 may be utilized in determinations conducted by computer 102, such as determinations relating to which exercise programs are presented to user 124. In one embodiment, device 326 may also wirelessly interact with a mobile device, such as device 138 associated with user 124 or a remote website such as a site dedicated to fitness or health related subject matter. At some predetermined time, the user may wish to transfer data from the device 326 to another location.

As shown in FIG. 3, device 326 may include an input mechanism, such as a depressible input button 328 assist in operation of the device 326. The input button 328 may be operably connected to a controller 330 and/or any other electronic components, such as one or more of the elements discussed in relation to computer 102 shown in FIG. 1B. Controller 330 may be embedded or otherwise part of housing 332. Housing 332 may be formed of one or more materials, including elastomeric components and comprise one or more displays, such as display 334. The display may be considered an illuminable portion of the device 326. The display 234 may include a series of individual lighting elements or light members such as LED lights 334 in an exemplary embodiment. The LED lights may be formed in an array and operably connected to the controller 330. Device 326 may include an indicator system 336, which may also be considered a portion or component of the overall display 334. It is understood that the indicator system 336 can operate and illuminate in conjunction with the display 334 (which may have pixel member 335) or completely separate from the display 334. The indicator system 336 may also include a plurality of additional lighting elements or light members 338, which may also take the form of LED lights in an exemplary embodiment. In certain embodiments, indicator system may provide a visual indication of goals, such as by illuminating a portion of lighting members 338 to represent accomplishment towards one or more goals.

A fastening mechanism 340 can be unlatched wherein the device 326 can be positioned around a wrist of the user 124 and the fastening mechanism 340 can be subsequently placed in a latched position. The user can wear the device 226 at all times if desired. In one embodiment, fastening mechanism 340 may comprise an interface, including but not limited to a USB port, for operative interaction with computer 102 and/or devices 138, 140.

In certain embodiments, device 326 may comprise a sensor assembly (not shown in FIG. 3). The sensor assembly may comprise a plurality of different sensors. In an example embodiment, the sensor assembly may comprise or permit operative connection to an accelerometer (including in the form of a multi-axis accelerometer), a gyroscope, a heart rate sensor, location-determining device (e.g., GPS), light sensor, temperature sensor (including ambient temperature and/or body temperature), heart rate monitor, image-capturing, such as a GPS sensor, moisture sensor and/or combinations thereof or other sensors. Detected movements or parameters from device's 142 sensor(s), may include (or be used to form) a variety of different parameters, metrics or physiological characteristics including but not limited to speed, distance, steps taken, and energy expenditure such as calories, heart rate and, sweat detection, effort, oxygen consumed, and/or oxygen kinetics. Such parameters may also be expressed in terms of activity points or currency earned by the user based on the activity of the user. Examples of wrist-worn sensors that may be utilized in accordance with various embodiments are disclosed in U.S. patent application Ser. No. 13/287,064, filed on Nov. 1, 2011, the contents of which are incorporated herein in their entirety for any and all non-limiting purposes.

Figure 1C:
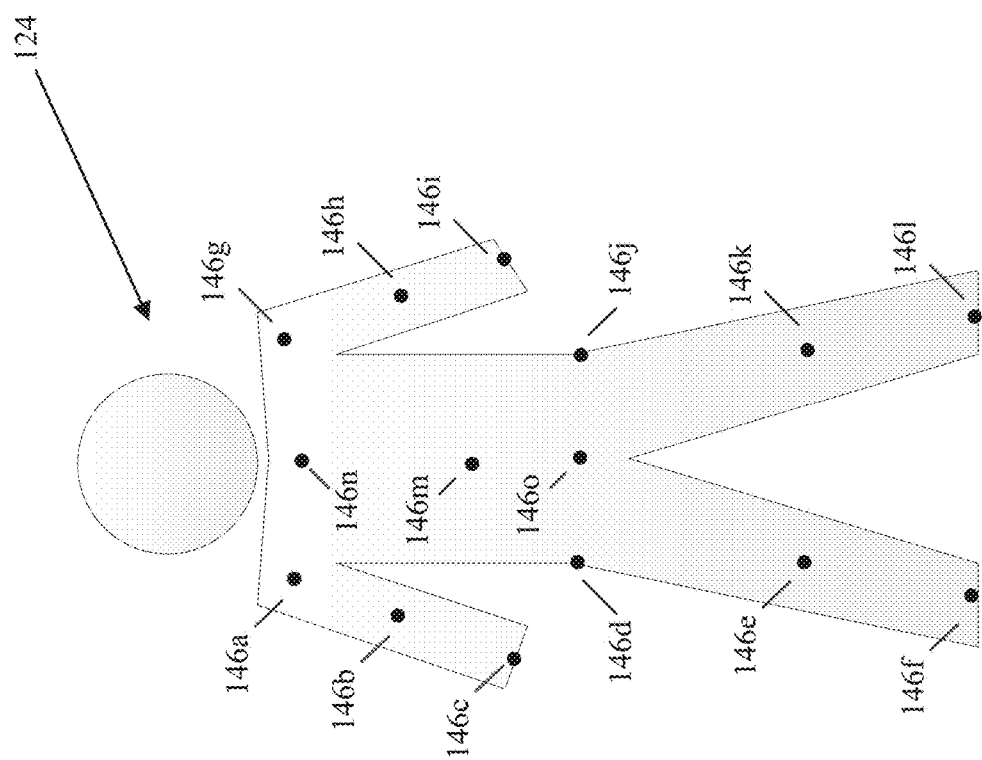

FIG. 1C shows illustrative locations for sensory input (see, e.g., sensory locations 146a-146o). In this regard, sensors may be physical sensors located on/in a user's clothing, yet in other embodiments, sensor locations 402a-402o may be based upon identification of relationships between two moving body parts. For example, sensor location 146a may be determined by identifying motions of user 124 with an image-capturing device, such as image-capturing device 126. Thus, in certain embodiments, a sensor may not physically be located at a specific location (such as sensor locations 146a-146o), but is configured to sense properties of that location, such as with image-capturing device 126 or other sensor data gathered from other locations. In this regard, the overall shape or portion of a user's body may permit identification of certain body parts. Regardless of whether an image-capturing device, such as camera 126, is utilized and/or a physical sensor located on the user 124, and/or using data from other devices, (such as sensory system 202), device assembly 226 and/or any other device or sensor disclosed herein or known in the art is utilized, the sensors may sense a current location of a body part and/or track movement of the body part. In one embodiment, sensory data relating to location 146m may be utilized in a determination of the user's center of gravity (a.k.a, center of mass). For example, relationships between location 146a and location(s) 146f/146l with respect to one or more of location(s) 146m-146o may be utilized to determine if a user's center of gravity has been elevated along the vertical axis (such as during a jump) or if a user is attempting to "fake" a jump by bending and flexing their knees. In one embodiment, sensor location 146n may be located at about the sternum of user 124. Likewise, sensor location 146o may be located approximate to the naval of user 124. In certain embodiments, data from sensor locations 146m-146o may be utilized (alone or in combination with other data) to determine the center of gravity for user 124. In further embodiments, relationships between multiple several sensor locations, such as sensors 146m-146o, may be utilized in determining orientation of the user 124 and/or rotational forces, such as twisting of user's 124 torso. Further, one or more locations, such as location(s), may be utilized to as a center of moment location. For example, in one embodiment, one or more of location(s) 146m-146o may serve as a point for a center of moment location of user 124. In another embodiment, one or more locations may serve as a center of moment of specific body parts or regions.

II. Systems and Methods for Conducting Joint Workouts

Further aspects of this disclosure relate to systems and methods for conducting a joint workout between two or more remote users, such as user 124 and another individual located at a location that is not viewable from the location user 124 is located.

In one embodiment, user 124 may be located at a first physical location, such as their home, and a second user may be located at a second physical location, such as a gym, dwelling, school, or even exercising outside, such as running through a city. Yet in another embodiment, user 124 may be located in a first area at a first location (e.g., a dwelling) and the second user is located at a second area at the same location. For example, user 124 may be located in a bedroom of the dwelling and the second user is located in a living room of the same physical dwelling. In yet another embodiment, at least one of the users may be outside and may travel amongst different locations during a joint workout. For example, the second user may begin the workout at the first dwelling but travel outside (and possible into another dwelling or structure) during the joint workout.

Certain aspects of this disclosure relate to a graphical user interface (UI) configured to facilitate a joint session of two or more remote users. Despite being at different physical locations, users may still compete and/or collectively engage in athletic activities. In one embodiment, each of a plurality of users may engage in a competition in substantially real-time. Yet, in other embodiments, a first user may conduct a predefined series of activities or routines and data from that first user's performance may be utilized in a later conducted competition. In one embodiment, two or more users may engage in a "side-by-side" competition. Thus, aspects of this disclosure relate to system and methods that may simultaneously present a UI, such as UI 402 on two remote display devices in which the users may conduct a joint session despite being remotely located.

Figure 4A:
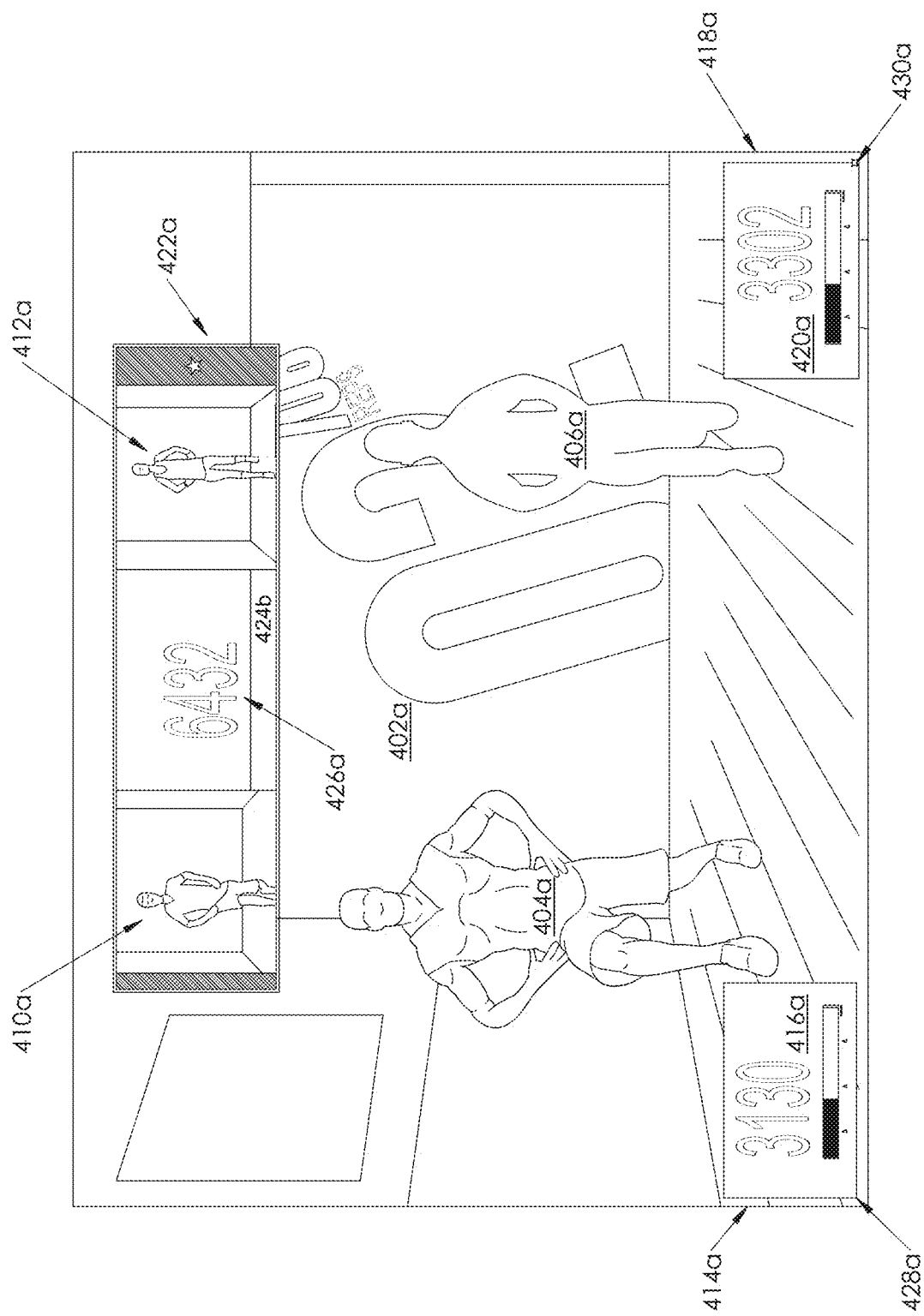
Figure 4B:
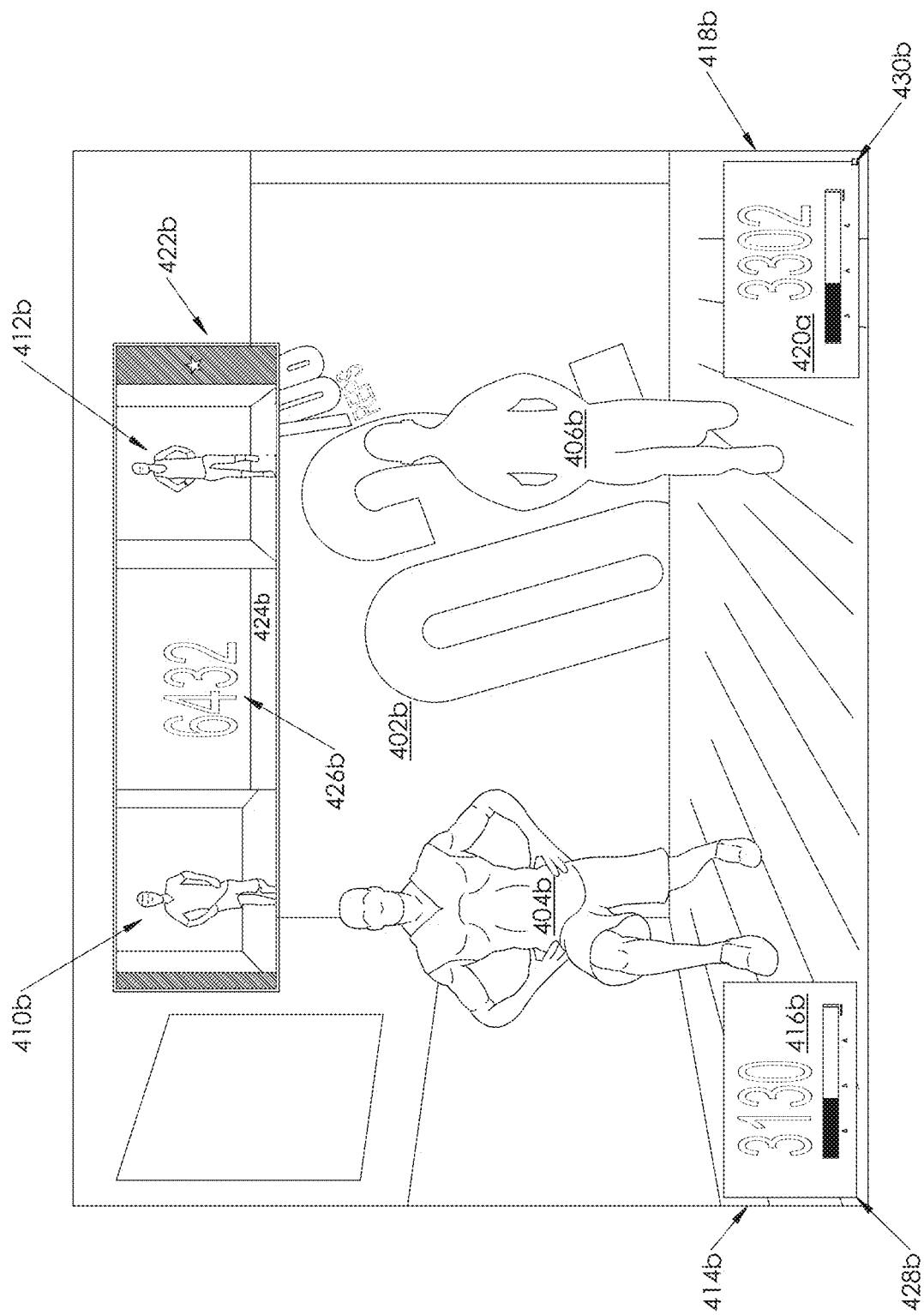
Figure 5:
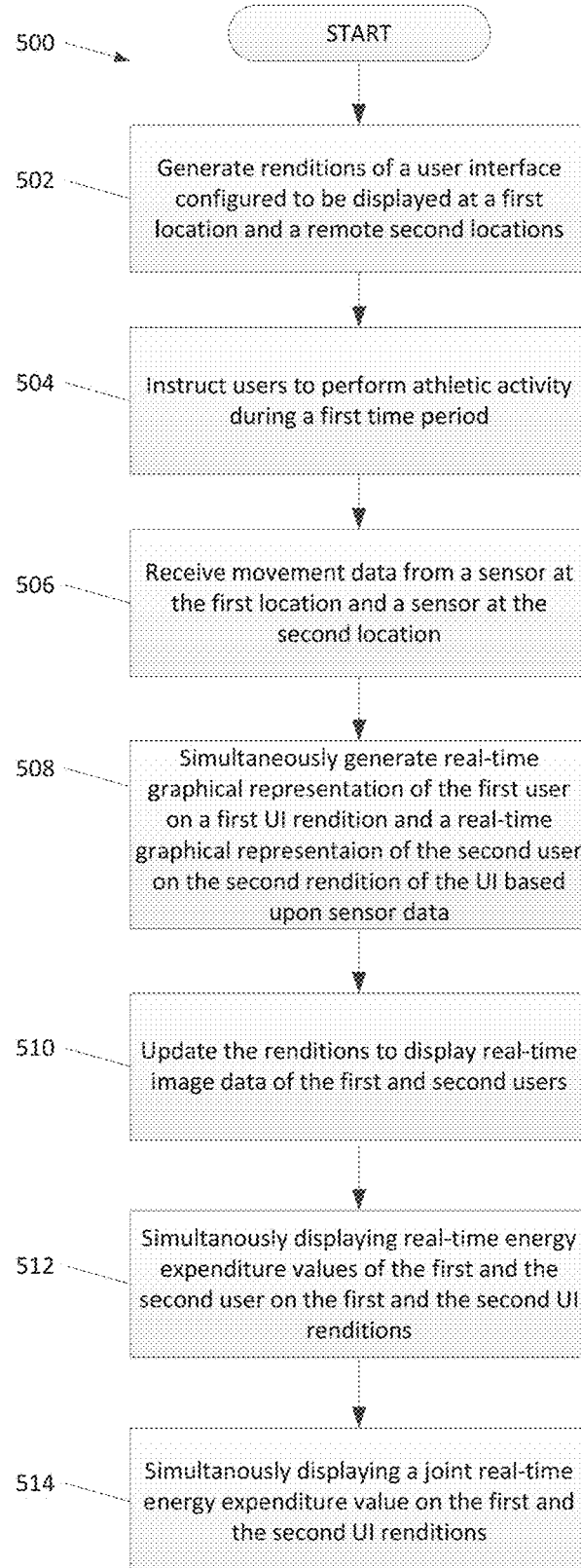
FIG. 5 is a flowchart of an example method that may be utilized to conduct a joint workout session between multiple remote users in accordance with an example embodiment.

In accordance with one embodiment, computer-executable instructions stored on a non-transitory computer-readable medium may be configured, such that when executed by a processing unit 106, cause the generations of a user interface (UI) to be displayed on multiple remote display devices. FIGS. 4A-B show an illustrative UI 402 that may be implemented in accordance with various embodiments. As shown in FIG. 4A, UI 402a is displayed on a display device, such as device 136, viewable by the first user 124. The generation of various iterations of a user interface may be based, at least in part, upon athletic movements of two or more users located in remote locations. FIG. 5 shows a flowchart 500 that provides one illustrated method that may be utilized in accordance with various embodiments. The exemplary method of flowchart 500 may be utilized with one or more user interfaces, including but not limited to UI 402 shown in FIG. 6.

In one embodiment, multiple renditions of a user interface (e.g., UI 402) may be generated and configured to be displayed at least two different locations or display devices (see, e.g., block 502 of FIG. 5). For example, UI 402b may be configured to be displayed on a second display device in the viewable range of a second user. As shown in FIG. 4B, UI 402b shows an illustrative corollary rendition of UI 402a that may be configured to be shown to a second user (not user 124) which may be at a second location. In certain embodiments, renditions of UI 402a/b may be altered, modified or otherwise adjusted based upon a plurality of factors, including but not limited to, the location of one or more users, user preference, data obtained from one or more sensors, and combinations thereof. The generation of various iterations of a user interface may be based, at least in part, upon athletic movements of two or more users located in remote locations. In certain embodiments, rendition of UI 402b may be configured to be simultaneously displayed at the second location as the rendition of UI 402a is provided at the first location such that UIs 402a/402b are synchronized. As used herein, "simultaneously" does not exclude delays that are inherent in the transmission of data between two or more nodes and/or storage of information on a non-transitory computer-readable medium. In this regard, those skilled in the art will realize that variations in network speed, points of congestion, and other inherent delays known in the art. Thus, recitations of simultaneous occurrences include delays for transmitting data, including electronic signals instructing one or more users to start or stop performing athletic movement. Similarly, references herein the "real-time" occurrences do not require exact precision and those skilled in the art will realize that inherent delays may be present in executing "real-time" actions or occurrences.

Renditions of UI 402 may comprise at least a portion of the same elements as each other. For example, UI 402b is shown as having substantially the same (or identical) elements as rendition of UI 402a.

In accordance with certain embodiments, two or more user users 124/125 may be instructed to perform at least one exercise during a joint session, in which UI renditions 402a/402b are shown to the respective users. (See, e.g., block 504 of FIG. 5). One or more embodiments may comprise a virtual trainer, such as trainers 404a/404b, associated with UI 402a/b to provide guidance or instructions to users 124 and 125. The rendition of virtual trainer 406a/406b (including form, action, appearance and any other feature) may be controlled, at least in part, according to computer-executable instructions stored on one or more a non-transitory computer-readable mediums. For example, the attributes of virtual trainer rendition 404a (including attributes not explicitly shown in FIGS. 4A-B) may be based on computer-executed instructions stored on a first computer-readable medium, such as memory 108, and attributes of rendition 404b may be based, at least in part instructions stored on a second computer-readable medium, which may be remotely located from memory 108. In this regard, each user 124/125 may have a different virtual trainer with one or more different virtual qualities. For example, user 124 may select a female trainer while user 125 may select a male virtual trainer. In yet other embodiments, one or more users may have the same virtual trainer (such as a specific female virtual trainer), however the trainer's attributes may be altered based upon the user's movements or preferences. For example, virtual trainer 404a may provide more feedback (such as through a virtual voice) to user 124 and/or may provide further movements or guidance if user 124 appears to be struggling with a certain instruction.

Virtual trainer renditions 404a/404b may be configured to simultaneously prompt the remote users to perform a specific exercise. For example, one or more devices may cause the respective displays to present a virtual trainer rendition 404a/b demonstrating an exercise to instruct the users 124/

125. For example, renditions 404a/404b may each be synchronized such that, virtual trainer 404a is performing the same athletic movement (or portion thereof) at the same time that virtual trainer 404b is performing that athletic movement (or portion thereof). Trainers 404a/404b may be configured to simultaneously perform the athletic movement at the same predetermined tempo during the first time period as each other, such that simultaneous actions of users 124/125 may be directly correlated. This may further allow detection of how each user 124/125 may be performing with respect to the tempo and/or other attribute of trainer 404a/ 404b.

As one example, virtual trainers 404 may be rendered on the respective displays performing an exercise at multiple positions. Directional cues, such as arrows may be utilized to instruct a user in which direction to move. UI renditions 402a/b may be configured to present an animation of the virtual trainer 404a/b demonstrating proper form for performing a repetition of an exercise (e.g., a slow lunge). In addition to, or instead of, a virtual trainer 404a/b, the UI 402a/b may be configured to present a depiction and/or an actual video of a real person demonstrating proper form for an exercise.

Figure 6:
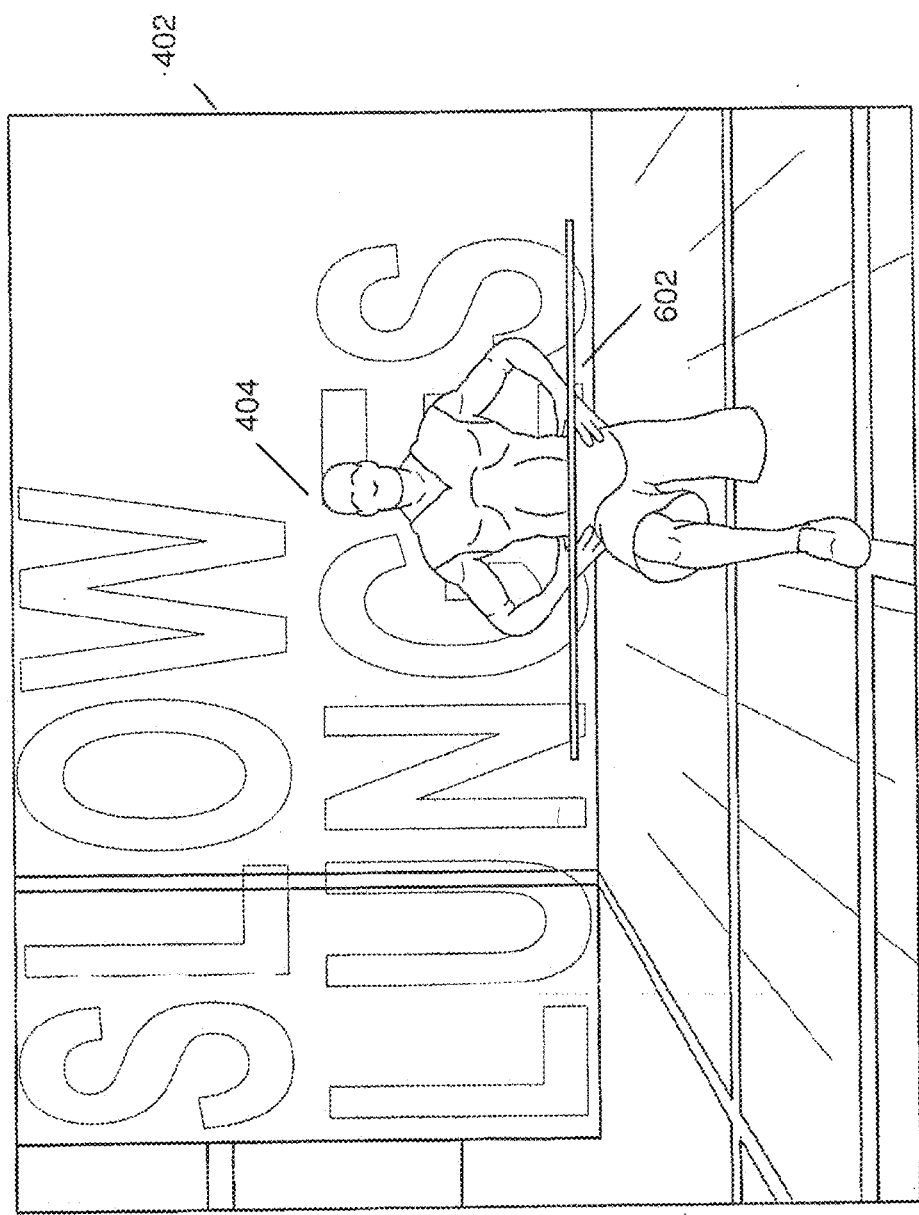
FIG. 6 provides an example UI interface that may be utilized to provide form guidance in accordance with on exemplary embodiment.

Form guidance information may also be provided. FIG. 6 provides an example of one embodiment in which UI 402 provides form guidance. Form guidance information 602 may be presented on (or otherwise associated with) the virtual trainer 602 or a graphical representation of user 124 when demonstrating an exercise. Form guidance information 602 may be a straight line, an angle between lines, or other information to guide the user about proper form for an exercise. In FIG. 6, for instance, form guidance information 602 is a straight line across a user's hip bones instructing the user to keep their hips level relative to the floor. Form guidance information may be provided through feedback mechanisms that do not include graphical or textual data overlaid on an avatar, such as virtual trainer 602. In this regard, form guidance information may include audio or tactile information. For example, voices or sounds may provide an indication of how straight a user's hips are (or are not). In another embodiment, a signal may be provided to a device, such as sensor device(s) 138, 140, 142 and/or 144 to provide vibrational output configured to be felt by user 124 to provide guidance. For example, a vibration may be provided to the sensor device 138 upon determining that the user's hips are not straight.

In this regard, form guidance provided on UI rendition 402a may be different than form guidance provided on UI rendition 402b. In one embodiment, at least one rendition of UI 402 does not comprise any form guidance. In another embodiment, form guidance may be provided based upon the respective user performance. For example, form guidance may be based upon one or more of: past user performance, current user performance, user preferences, goals, parameters of the joint session, and/or a combination thereof among other factors that would be appreciated by a person of skill in the art.

Further aspects of this disclosure relate to generating and updating a UI, such as UI 402, based upon real-time fitness or movement data obtained from two or more users that are located at different locations (see, e.g., block 506 of FIG. 5). In accordance with one embodiment, various devices (e.g., computer 102) may prompt the users to move into a certain region relative to a device, such as display 136, capturing device 126 and/or relative to the sensor 128, so that the user is within frame and/or range. Prompting of at least one user may be done, for example, through virtual trainer 404a. When properly positioned, the system 100, through one or more sensors, may process movement of the user 124. In certain embodiments, the UI rendition 402a may only show the graphical representation of the local user (e.g., representation 406a user 124) inclusive of any adjustments based upon the user's real-time movements and not other graphical representations of other remote users, (e.g., representation 406b of user 125).

In an example, the system 100 of FIG. 1 may include more than one sensor, such as image capturing device 126, and may capture video from different perspectives. One or more devices, such as computer 102, may process some or all images and/or infrared data to create one or more user avatars as representations 406a/406b. In this manner, display 136 may present a user's form from multiple angles for the user to observe. Yet, in other embodiments, data for different angles may be derived from one or more sources. For example, the image capturing device 126 may be positioned at any desired angle relative to a user performing an exercise, such as, for example, at least one of a front view, left side view, a right side view, and a back view of a user. In another example, the system 100 may include more than one infrared device 128 to capture infrared reflections of the user 124 from different perspective. Also, the system 100 may include both an image capturing device 126 and an infrared transceiver 128 (or more than either one or both) positioned at different/various locations and/or any other sensors disclosed herein, which may be utilized in the generation and/or rendering of representations 406a/406b. Graphical representations 406a/406b may be generated from sensors that lack any image capturing capabilities. For example graphical representation 404a may be generated from user 124 wearing devices 138, 140, 142, and/or 326. In one embodiment, graphical representation 404a may be generated entirely on accelerometer and/or gyroscope sensor data. Those skilled in the art will appreciate that other sensors, alone or in combination, may be utilized to generate graphical representations 406a/406b.

Representations 406a/406b may be generated or displayed based upon the respective user's real-time movement (See, e.g., block 508 of FIG. 5). For example, user(s) 124/125 may each be positioned in range of a sensor, such as in front of the image capturing device 126 and/or sensor 128, which may comprise an infrared transceiver. Display 136 may present UI 402a comprising representation of user 124 that may be a "mirror-image" or depict a virtual avatar, such as a user avatar, that moves to correspond with user movement. A different display may present UI 402b to user 125 based on similar factors. A graphical representation (e.g., representation 406a of FIG. 4A) of the local user may be different from the graphical representation configured to be displayed to another user. For example, the remote UI rendition 402b of FIG. 4B may be configured to be presented to the second user 125 and may be configured to display representation 406b (which may be displayed in substantially the same orientation and/or location as 406a shown in FIG. 4A), however may represent the second user rather than the first user 124. In this regard, various renditions of UI 402 (such as renditions 402a/402b) may comprise only a real-time graphical representation of the local user and not another user.

Further aspects of this disclosure relate to the simultaneous display of real-time image data of a plurality of users associated with the joint session on a single display device (see, e.g., block 510 of FIG. 5). For example, UI rendition 402a (which may be configured to be displayed to user 124 at the first location) may comprise video data 410a which is configured to display a live video feed of user 124 and video data 412*b* which is configured to display a live video feed of user 125 located at the second location. Similarly, UI rendition 402*b* may also be configured to simultaneously show video data 110*b*/112*b*. In certain embodiments, 110*a* and 110*b* and/or 112*a* and 112*b* may be identical; such as multiple users 124/125 have a live video feed of themselves at least one remote user. The rendered real-time image data 110*a*/110*b* may be provided in combination with or, as an alternative to the display of the graphical representations of the users (rendered as 404*a/b*) and/or virtual trainer renditions 406*a/b*.

Thus, certain embodiments encompass implementations of a UI 402*a* rendered to a first user 124 at a first location that includes a graphical representation of that user 124 (e.g., rendition 406*a*) displayed simultaneously with image data 410*a* of the same user 124 and a second remote user (e.g., image data 412*a* of user 125) along with a rendered virtual trainer 404*a* that instructs the user 124 to perform a specific physical movement. Simultaneously, the UI 402 may be rendered to a second user 125 located at a second location (rendition 402*b*) that includes image data of the first and second users 124/125 (see image data 410*b* and 412*b*) and with a rendered virtual trainer 404*b* that instructs the second user 125 to perform the same physical movement as virtual trainer rendition 404*a* provided to user 124. Therefore, in accordance with one embodiment, the first rendition of the user interface 401*a* is configured to simultaneously:
(1) display virtual trainer 404*a* performing the athletic movement at a first tempo that is synchronized with the tempo of a second virtual trainer 404*b* configured to be displayed simultaneously to a remote user 125; and
(2) display the real-time graphical representation of the first user performing the athletic movement based upon the at least one sensor at the first location.

Including image data (which may comprise a live feed) of multiple users on the single display device may provide one or more benefits not realized in the prior art. Seeing image data of another user may provide motivation to work harder or increase the session's duration. Further, users 124/125 may utilize facial expressions or body language to determine if their competitor or teammate is getting tired or otherwise determine their fitness abilities. In certain embodiments, image data 110/112, either alone or in combination with audio capabilities, may provide increased social aspects. In this regard, increased social interactions may provide incentives for remote users to engage in physical activities, either as a competitive nature, friendly nature and/or as a team.

Further aspects of this disclosure relate to displaying substantially real-time calculations of energy expenditure. Energy expenditure may be calculated by one or more methods. In certain embodiments, energy expenditure calculations may be based, at least in part, on the sensors, and or environment of the respective user(s). For example, in additional to processing the images, sensor data, and infrared data, computer 102 may receive data from other sources. For example, the user may run a predetermined distance as measured by a sensor attached to the user (e.g., sensor in a shoe) or global positioning system (GPS) device and may upload the data to computer 102. Computer 102 may compare the captured data to desired data for each exercise to monitor the user's form while performing an exercise. The desired data may include multiple comparison points throughout an exercise, and/or locations of various body parts during the exercise. For example, a push up may be divided into four events: (1) the lowest point where the user's chest is nearest to the ground or other reference point and/or their arms are bent at a maximum bend; (2) a highest point where the user's chest is farthest from the ground and/or their arms are straightened (e.g., a maximum straightness); (3) an upward event where the user transitions from the lowest point to the highest point; and (4) a downward event where the user transitions from the highest point to the lowest point.

The desired data may specify comparison points for each of these events focusing on certain body parts. For example, at each comparison point during a pushup, computer 102 may monitor the spacing of the user's hands, the straightness of the user's back, a location of the user's head relative to their torso, the spacing of the user's feet relative to one another, or other aspects. The desired data may specify desired locations for each body part being monitored during comparison points for an exercise, as well as permitted variations from the desired locations. If the user's body part varies beyond what is permitted, computer 102 may provide the user with feedback identifying the body part and a correction to the user's form (e.g., back is arched, and not straight, during a pushup). Exemplary methods of determining energy expenditure are provided in U.S. Provisional Patent Application 61/655,365 filed Jun. 4, 2012, the contents which are incorporated herein by reference in their entirety for any and all non-limited purposes.

If an exercise session involves different types of exercises, determinations of points, including but not limited to energy expenditure points may be based on the type of exercise. The type of sensors utilized to determine points may fluctuate based upon the specific exercise and/or the user's performance of the exercise. In further embodiments, energy expenditure (e.g., a quantity of calories burned) may be ranked as percentage over an ideal value or range for an exercise or routine.

For example, if perfectly performing an exercise would burn about 100 calories, a first user who burned 90 calories may be assigned a better ranking than second user who only burned 85 for the same exercise. The users could have different ideal values or ranges, thus the determinations may utilize the percentage of the detected and/or estimated values as a percentage for that user's ideal value. In further embodiments, a user who is closer to 100% of their ideal value may be ranked higher than users who have over 100% of the ideal quantity of calories burned. In this regard, a user who expends more energy than estimated or calculated for an activity (e.g., exercise) may indicate improper movements, inefficiency, increased likelihood of injury, and/or combinations thereof.

System 100 may also determine calories expended from graphical renditions, image data, including, pre-recorded videos or from the image data 110/112*b*. One or more components of system 100 may process the video to determine locations of a center of mass of the player, or of particular body parts, at various points in time, and determine the amount of calories expended during the physical activity (e.g., by the player during the dunk) using the work-based calorie determination, described above.

In accordance with one embodiment, calculated energy expenditure determinations based upon the respective users 124/125 real-time performances may be simultaneously displayed on a user interface (see e.g., block 512 of FIG. 5). As one example, interface 414*a* may comprise a real-time indication of energy expenditure of user 124 (and interface 414*b* may be the same indication shown on rendition 402*b*). For example, interface 414 may comprise energy expenditure values 416. In one embodiment, value 416 may represent a calculated energy expenditure value and/or other value of a point system specific to the physical movements of user 124. Interface 418a may be simultaneously displayed with interface 414a and comprise a calculated value (e.g., value 420a) associated with the movements of user 125. For example, in certain embodiments, interfaces 414a and 418a may be updated in real-time to reflect values (such as an energy expenditure value) associated with the respective movements of users 124 and 125 responsive to the instructions provided by virtual trainers 404a and 404b. Thus, according to certain implementations, a plurality of users (e.g., users 124/125) may readily view not only which user has the highest value, or the energy expended per unit time, but also determine how close the other user's value is to theirs, whether the other user(s) are getting closer or further, and/or determinations relating to other users performances on specific routines. As seen in the illustrative embodiment, interfaces 414 and 418 may be provided on a single interface (e.g., interface rendition 402a comprises 414a and 418a), however, the interfaces may be located in different areas of UI 402 for specific renditions, such as renditions 402a and 402b. Further, the appearance and/or operation of interface 414 and/or 418 or any other element of UI 402 may be different amongst different renditions.

In certain embodiments, a graphical indication may be associated with the user(s) who currently has the highest quantity of points (see, e.g., indication 422). In certain embodiments, indication 222 or another indication may be utilized to indicate the user(s) earning the most points per unit time, points awarded for difficult movements, best performance of a specific movement, matching the form, tempo or other attribute set forth by the virtual trainer or combinations thereof.

Still yet further embodiments, an interface, such as interface 224, configured to display a joint total of points determined from the joint movements of at least two users, such as users 124 and 125. In the illustrative embodiment, interface 424a comprises value 426 which is calculating from combining the points of user 124 (set forth in interface 414a) and user 125 (set forth in interface 418). Value 426 may be updated in real-time (see, e.g., block 514 of FIG. 5). Although interface 224 is shown separate from interface 414 and 418, those skilled in the art will appreciate that interface 424 or any other element may be part of another interface, such as any other elements disclosed herein.

Figure 7:
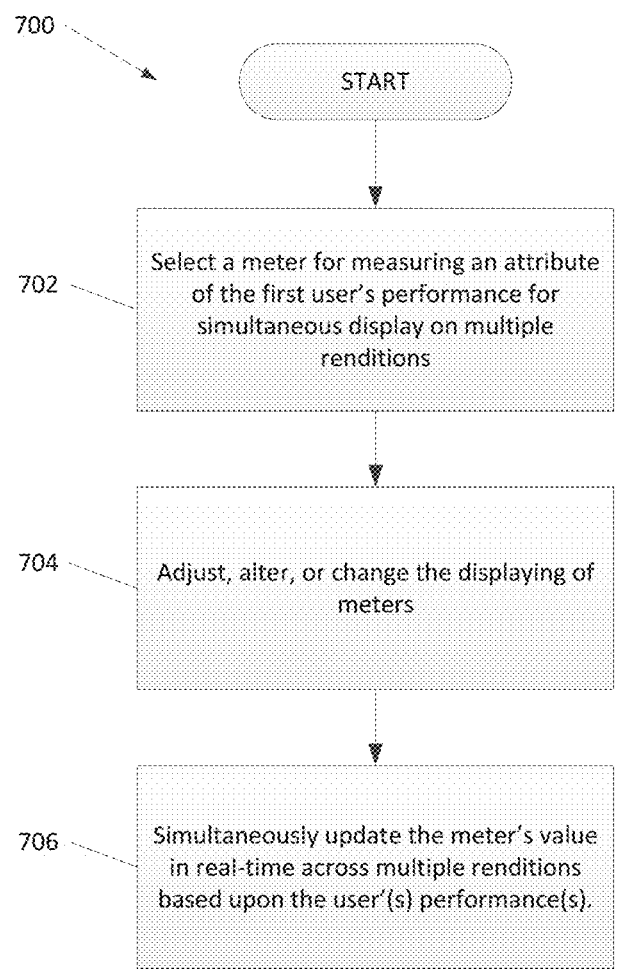
FIG. 7 is a flowchart of an exemplary method of selecting and updating a meter in accordance with one embodiment.

For example, looking to FIG. 4A, rendition 404a comprises meter 428a. FIG. 7 is a flowchart of an exemplary method of selecting and updating a meter in accordance with one embodiment. As one example, meter 428a may be selected based upon the type of athletic movement demonstrated by virtual trainer 404a (see, block 702 of FIG. 7). In one embodiment, if the activity to be demonstrated by trainer 404 (and/or performed by user 124) is known or considered to be a good indication of measuring cardiovascular health, then cardio meter 428a may be displayed on UI 402a/402b during the user's 124 performance of the activity (see also, meter 428b shown remotely on FIG. 4B). Similarly, meter 430a may be simultaneously displayed on UI rendition 404a to user 124. Meter 430a may relate to the performance of the athletic activity by user 125.

Meters 430a/430b are not limited to cardio meters. For example, in one embodiment, if the predetermined athletic activity is considered or known to be a good indication of measuring strength, then a strength meter may be selected for display on UI 402a/402b during the user's performance of the activity. Those skilled in the art will readily appreciate that a strength meter and a cardio meter are merely examples, and that other meters may be among the plurality of meters. Block 704 may be implemented to adjust, alter, or entirely change the display properties of the selected meter. In this regard, block 704 may be implemented to perform one or more of: determine which renditions of UI are configured to display the selected meter, whether the selected meter is the only meter, selection of an additional meter, and combinations thereof. In certain embodiments, more than one meter may be simultaneously displayed on UI 402a/402b. For example, either by default, user preference, and/or other factors, a strength meter and a cardio meter may each be configured to be simultaneously displayed on at least one user's rendition of UI 402.

In one embodiment, a user 124 may determine which meter is shown on each user's UI 402 (which may occur as part of blocks 702 and/or 704). For example, if it is decided (either by default computer-executable instructions, or indirectly through user input) that a "winner" of a specific competition between two or more users is to be decided according to a specific attribute (e.g., strength, cardio, fitness, athleticism, speed, tempo, etc.), then a specific meter may be selected based upon this determination. In certain embodiments, scoring may be based upon scaling or otherwise combining multiple attributes, therefore, multiple meters may be available for selection (or automatically selected).

In yet another embodiment, selections (such as part of block(s) 702/704) may be based upon a user's performance. For example, if user 124 is "winning," such as by having a higher cumulative value of energy expenditure points (which may be updated in real-time as value 416), then the selection and/or display properties of a meter may be based upon this. For example, if user 124 is currently performing better than a remote user 125 as measured by "strength" but not "cardio," then the strength meter may be selected for display. In yet another embodiment, user 124 may select a specific meter to be shown based upon a pre-inputted user input.

In one embodiment, a plurality of different meters may each relate to a single user's performance. For example, a strength meter and a cardio meter specific to a user's performance may be simultaneously displayed on rendition 404a. The displaying and updating of one or more meters 428a specific to a single user's performance may be simultaneously displayed on the same UI rendition 404a with one or more meters specific to a remote user's 125 performance. Further, in certain embodiments, certain meters may be selectable to be displayed only on a local user's UI rendition 402a. However, in other embodiments, both UI renditions 402a/402b may comprise the selected meter(s). Users 124/125 may be permitted to select which meters 428/430 are displayed to another user 124/125.

The meter(s) may be updated in real-time as the users perform the predetermined athletic activity (see, e.g., block 706). Thus in certain embodiments, each of a plurality of users remotely located from at least one other user may compare their performance with at least one other user. The updating of the meter(s) 428/430 may be based upon sensor data, such as described herein. In one embodiment, the properties of at least the first selected meter may be based upon data received from the at least one sensor located at the first location and simultaneously altering the properties of the second selected meter based upon data received from the at least one sensor at the second location.

Figure 8A:
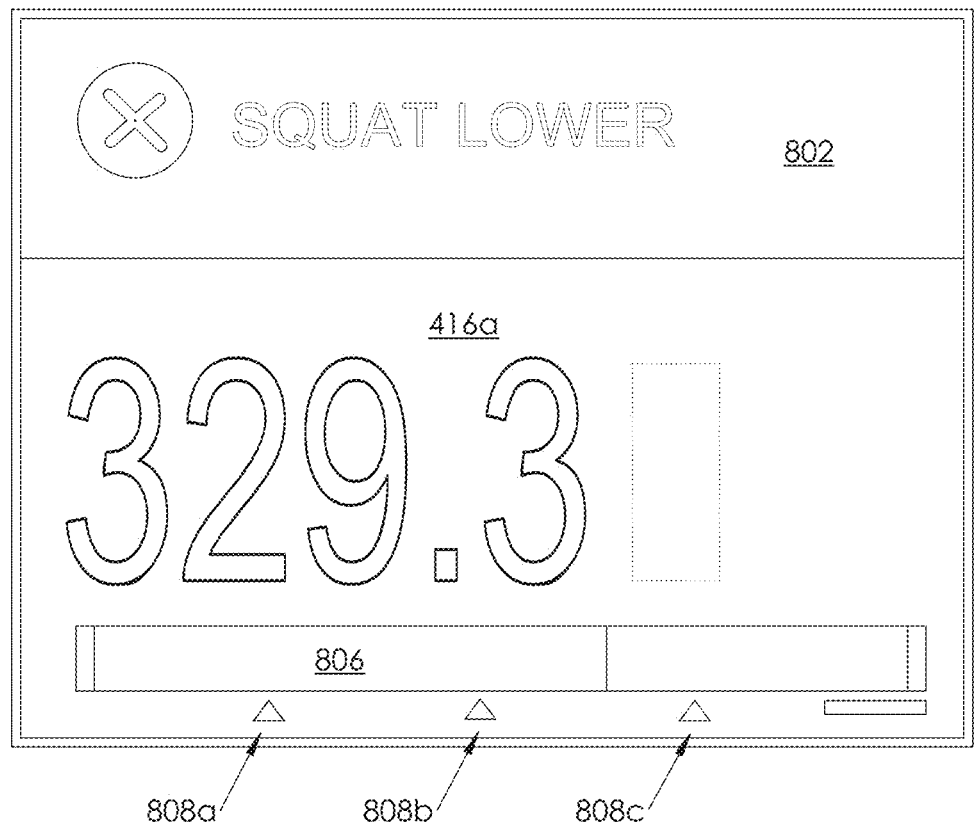
FIGS. 8A-B show example meters that may be utilized in accordance with various embodiments disclosed herein. Specifically.
Figure 8B:
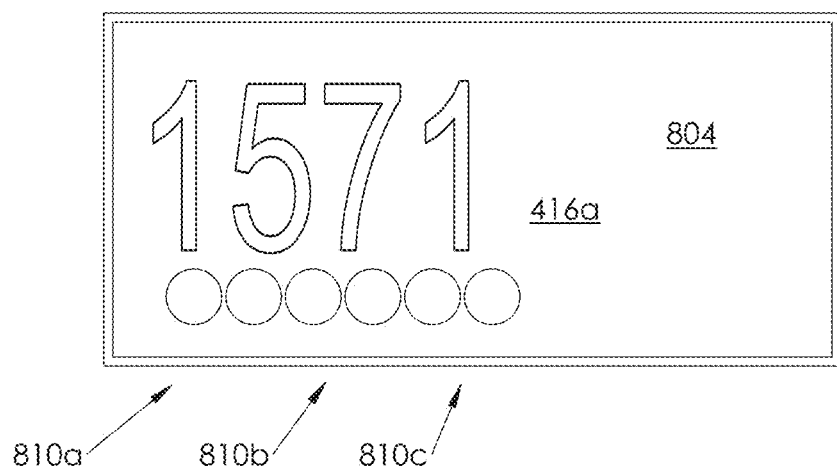

FIGS. 8A-B show example meters that may be utilized in accordance with various embodiments disclosed herein. Specifically, FIG. 8A shows an example cardio meter 802 and FIG. 8B shows an example strength meter 804.

Although the examples are discussed in the context of illustrative meters 802/804, those skilled in the art will appreciate that other meters may be implemented without departing from the scope of this disclosure. One or more of meters 802/804 may be configured to be displayed on UI renditions 402a/402b, such as for example but not limited to interface(s) 414/418. As such other values, such as energy expenditure values 416/420 or other points may be displayed proximate to one or more of meters 802/804, including on the same interface 414/418.

In one embodiment, cardio meter 802 (which is usually the blue bar shown below) may comprise a measuring bar 806 (or other structure or shape) that may "fill" or otherwise be visually adjusted based on an intensity attribute of the user's physical movements. The adjustment of measuring bar 806 may be directly based upon data received from sensors at the user's location. For example, in one embodiment, the movement of measuring bar 806 may be based upon the local user's movement intensity. In one embodiment, the more user 124 moves, the more measuring bar 806 will fill. In one embodiment, the movement of measuring bar 806 may be directly correlated to energy expenditure. In one such embodiment, energy expenditure value 416a may be directly correlated to the movement of measuring bar 806. In another embodiment, energy expenditure value 416a may be a cumulative tally of energy expenditure for a specific workout or portion thereof having a first time frame (such as 5 minutes), and measuring bar 806 may be correlated to energy expenditure directed towards a second time frame, which may be inclusive and/or overlap with the first time frame. For example, measuring bar 806 could provide feedback on the current real-time energy expenditure (e.g. the last second or few seconds) and thus be an indicator of explosiveness. In yet other embodiments, measuring bar 806 may provide feedback on a different period of time.

In other embodiments, energy expenditure value 416a and measuring bar may each relate to energy expenditure, however, are not correlated. For example, one of energy expenditure value 416a or measuring bar 806 may be configured to measure energy expenditure during an athletic movement (or multiple movements) while the other measures only those expenditures fitting a specific criteria. For example, UI 402 may be configured such that the measuring bar 806 (or value 416a) may only be updated to display energy expenditure (or another attribute) based on proper movements. For example, if a virtual trainer 404a is instructing user 124 to perform a lunge and user 124 is performing a push up, at least a portion of user's 124 movements may not be considered in updating one or more meters or values. Similarly, the timing of the user's 124 movements may reflect which, if any values, such as value 416a, or meters, such as meters 802/806 are updated to reflect the actual movement. For example, if trainer 404a instructs user 124 to perform jumping jacks at a rate of 1 jumping jack per 2 seconds and the user is performing jumping jacks at the rate of 1 per 4 seconds, then at least one meter or value may be updated such that at least some of the movements are not considered or are scaled by a scaling factor. As would be appreciated by those skilled in the art, value 416a may not be displayed and the discussion above applies equally to the functionality of meter 802 (or meter 804) even when displayed alone.

An area or length of measuring bar 806 may be based on a predetermined total. For example, a maximum value (e.g., filling of the entire measuring bar) may be based on one or more factors, such as but not limited to being 1) based upon user-specific data or 2) a universal standard. In this regard, certain users may be "handicapped" such that the display properties of meter 802/804 may be altered based upon their performance level.

Meter 802 (and/or another meter, such as meter 806) may comprise one or more markets associated with the measuring bar 804 or other property of the respective marker. For example, illustrative meter 802 comprises three arrowheads located on the lower portion of meter 802 (shown as arrowheads 808a, 808b, and 808c). In one embodiment, each successive arrowhead may represent a threshold. In certain embodiments, users may wish to perform at a certain performance level and thus the arrowheads 808a-808c may serve as a visual indication as such. For example, following performance of the athletic movement, computer-executable instructions may be executed to determine a performance level. In one embodiment, there may be for example 3 performance levels. Thus, in one embodiment, each successive arrowhead going from the left-most arrowhead (808a) towards the right-most arrowhead (808c) provides threshold levels for obtaining the next performance level.

In certain embodiments, a user may need to only pass the threshold set by the respective arrowhead, yet in other embodiments; the user must obtain a certain amount of time as being above a certain threshold level to obtain a reward of obtaining the next performance level. For example, the measuring bar 806 above the arrowheads 808a-808c may indicate the maximum value (e.g., a maximum energy expenditure value) that may be achieved for that specific movement (e.g., squat) and as the user conducts each of a plurality of successive squats, the measuring bar 806 fills and passes each of the three different thresholds set by the arrowheads 808a-808c. In another embodiment, the arrowheads 808a-808c may be used to indicating three different portions of the movement, such as each arrowhead may be correlated to a user conducting a different portion of the movement (e.g., moving downward, pausing, and then straightening back to an upward position). In one embodiment, a portion of measuring bar may be left unfilled, such as the portion between 808a-808b if a user did not meet a threshold level during the respective time period. Thus, in this respect, measuring bar may be viewed as a plurality of bars that each measure a specific period of time during a movement or among a plurality of successive movements.

Looking to FIG. 8B, meter 804 may be a strength meter configured to display (on one or more UI renditions, such as 402a and/or 402b), an indication of a user's performance based upon data from one or more sensors. Meter 804 may comprise a plurality of markers, such as the plurality of circular-shaped markers 810a-810c. In one embodiment, markers 810a-810c may serve one or more functions to those described in relation to markers 808a-808c discussed above in relation to FIG. 8A. In one embodiment, each successive marker (or a group of markers) may represent a threshold. In certain embodiments, users may wish to perform at a certain performance level and thus the markers 810a-810c may serve as a visual indication as such. In one embodiment, the determination of strength of a user may be determined according to their form as measured by one or more sensors. In this regard, a user's form during an athletic movement, such as a lunge or reps of lunges, may be compared to the ideal form. The ideal form may be demonstrated by a virtual trainer 404a that is simultaneously displayed on one or more UI renditions 404a/404b. In this regard, the virtual trainer may be performing the athletic activity at a predetermined tempo, thus the timing of the user's form may be considered in the determination of the attribute (e.g., strength) that may be simultaneously displayed at the local and remote UI renditions 404*a*/404*b*.

Similar to the discussion of the cardio meter 802, each marker (e.g., 810*a*-810*c*) may represent the user's cumulative strength or strength for successive portions or reps of athletic movements. Although meters 802 and 804 are described in context of a cardio and strength meters, respectively, those skilled in the art would readily appreciate that either meter may be modified to serve as the other without undo experimentation. For example, the bar of the cardio meter 802 could serve as the markers of meter 804 and vice-versa.

What is claimed is:

1. A computer-implemented method comprising:
   providing first instructions to a user to perform a first athletic movement;
   receiving, from a sensor, first activity data representing the first athletic movement by the user;
   calculating with a processor, based on the first activity data of the user, a first combinatory fitness-athleticism score;
   outputting, to a display device and in real-time, a first graphical interface indicating the first combinatory fitness-athleticism score;
   providing during a specific time frame, second instructions to the user to perform a second athletic movement;
   receiving, from the sensor, second activity data representing the second athletic movement by the user;
   calculating, with the processor, based on the second activity data of the user, a second combinatory fitness-athleticism score; and
   outputting, to the display device and in real-time, a second graphical interface indicating the second combinatory fitness-athleticism score and a meter that is selected based on an activity type of the second athletic movement,
   wherein the first and the second combinatory fitness-athleticism scores each comprise a fitness sub-score and a separate athleticism sub-score of the user,
   wherein the fitness sub-score is calculated, by the processor, using a first attribute comprising one or more of an endurance fitness attribute, a flexibility fitness attribute and a strength fitness attribute of the user,
   wherein at least one of the endurance fitness attribute, the flexibility fitness attribute, and the strength fitness attribute is determined by calculating calories burned during performance by the user, and
   wherein the second graphical interface displays a value of the first attribute used to calculate the fitness sub-score.

2. The computer-implemented method of claim 1, further comprising: providing an indication of an activity that the user can perform that will not cause injury, based upon the first and second combinatory fitness-athleticism scores for the user.

3. The computer-implemented method of claim 1, wherein the first athletic movement comprises predefined criteria, the method further comprising: providing the first instructions to the user to perform, during a first time period, the first athletic movement.

4. The computer-implemented method of claim 1, wherein the first instructions and the second instructions include a plurality of drills configured to test a plurality of fitness attributes of the user and a plurality of athleticism attributes of the user.

5. The computer-implemented method of claim 1, wherein the first instructions and the second instructions include a predefined ordering of drills that are configured to be provided to the user during a single workout session.

6. The computer-implemented method of claim 1, wherein the fitness sub-score is based upon a percentile rank of the user within a population of users.

7. The computer-implemented method of claim 1, wherein the athleticism sub-score is based upon a percentile rank of the user within a population of users.

8. The computer-implemented method of claim 1, wherein the athleticism sub-score is calculated by the processor, using one or more of a speed athleticism attribute, an agility athleticism attribute, a reaction athleticism attribute, a power athleticism attribute, and a balance athleticism attribute of the user.

9. The computer-implemented method of claim 8, wherein the power athleticism attribute includes an energy expenditure estimate determined utilizing a metabolic equivalent of task (MET) table for a type of an exercise that the user performs during an athletic performance by the user.

10. The computer-implemented method of claim 1, wherein the sensor comprises an accelerometer.

11. The computer-implemented method of claim 1, wherein the value of the first attribute is displayed within a graphical meter that is updated in real-time.

12. An apparatus configured to be worn by a user, comprising:
    a structure configured to be worn around an appendage of a user comprising a sensor configured to capture movement data from the appendage of the user;
    a processor; and
    a non-transitory computer-readable medium comprising computer-executable instructions that when executed by a processor cause the processor to perform at least:
    providing first instructions to the user to perform a first athletic movement;
    receiving first movement data captured from the sensor during the first athletic movement by the user;
    calculating, from the received first movement data of the user, a first combinatory fitness-athleticism score;
    outputting, to a display device and in real-time, a first graphical interface indicating the first combinatory fitness-athleticism score and a meter that is selected based on an activity type of the second athletic movement;
    providing during a specific time frame, second instructions to the user to perform a second athletic movement;
    receiving second movement data captured from the sensor during the second athletic movement by the user;
    calculating, from the received second movement data, a second combinatory fitness-athleticism score; and
    outputting, to the display device and in real-time, a second graphical interface indicating the second combinatory fitness-athleticism score,
    wherein the first and second combinatory fitness-athleticism score each comprise a fitness sub-score and a separate athleticism sub-score of the user;
    wherein the fitness sub-score is calculated using a first attribute comprising one or more of an endurance fitness attribute, a flexibility fitness attribute and a strength fitness attribute of the user,
    wherein at least one of the endurance fitness attribute, the flexibility fitness attribute, and the strength fitness attribute is determined by calculating calories burned during performance by the user, and
    wherein the second graphical interface displays a value of the first attribute used to calculate the fitness sub-score.

13. The apparatus of claim 12, wherein the sensor is a first sensor and the apparatus further comprises a second sensor configured to capture movement data and the computer-readable medium further comprises computer-executable instructions that when executed by the processor cause the processor to perform at least: utilizing movement data from the second sensor in the calculation of the first and second combinatory fitness-athleticism scores.

14. The apparatus of claim 12, wherein the sensor is a first sensor and the computer-readable medium further comprises computer-executable instructions that when executed by the processor cause the processor to perform at least: utilizing movement data captured from a second sensor that is located externally from the apparatus in the calculation of the first and second combinatory fitness-athleticism scores.

15. The apparatus of claim 12, wherein the sensor is a first sensor and the computer-readable medium further comprises computer-executable instructions that when executed by the processor cause the processor to perform at least: receiving the movement data from a second sensor located externally from the apparatus; and based upon the movement data from the second sensor, instructing the user to perform an athletic movement with a predefined criterion.

16. The apparatus of claim 12, wherein the sensor is an accelerometer.

17. The apparatus of claim 12, wherein the value of the first attribute is displayed within a graphical meter that is updated in real-time.

18. A computer-implemented method comprising:
providing first instructions to a user to perform a first athletic movement;
receiving, from a sensor, first activity data representing the first athletic movement by the user;
calculating with a processor, based on the first activity data of the user, a first combinatory fitness-athleticism score;
outputting, to a display device and in real-time, a first graphical interface indicating the first combinatory fitness-athleticism score;
providing after a specific time frame, second instructions to the user to perform a second athletic movement;
receiving, from the sensor, second activity data representing the second athletic movement by the user;
calculating, with the processor, based on the second activity data of the user, a second combinatory fitness-athleticism score; and
outputting, to the display device and in real-time, a second graphical interface indicating the second combinatory fitness-athleticism score and a meter that is selected based on an activity type of the second athletic movement,
wherein the first and the second combinatory fitness-athleticism scores each comprise a fitness sub-score and a separate athleticism sub-score of the user,
wherein the fitness sub-score is calculated, by the processor, using a first attribute comprising one or more of an endurance fitness attribute, a flexibility fitness attribute and a strength fitness attribute of the user,
wherein at least one of the endurance fitness attribute, the flexibility fitness attribute, and the strength fitness attribute is determined by calculating calories burned during performance by the user, and
wherein the second graphical interface displays a value of the first attribute used to calculate the fitness sub-score.

19. The computer-implemented method of claim 18, further comprising: providing an indication of an activity that the user can perform that will not cause injury, based upon the first and second combinatory fitness-athleticism scores for the user.

20. The computer-implemented method of claim 18, wherein the first athletic movement comprises predefined criteria, the method further comprising: providing the first instructions to the user to perform, during a first time period, the first athletic movement.

21. The computer-implemented method of claim 18, wherein the value of the first attribute is displayed within a graphical meter that is updated in real-time.

22. An apparatus configured to be worn by a user, comprising:
a structure configured to be worn around an appendage of a user comprising a sensor configured to capture movement data from the appendage of the user;
a processor; and
a non-transitory computer-readable medium comprising computer-executable instructions that when executed by a processor cause the processor to perform at least:
providing first instructions to the user to perform a first athletic movement;
receiving first movement data captured from the sensor during the first athletic movement by the user;
calculating, from the received first movement data of the user, a first combinatory fitness-athleticism score;
outputting, to a display device and in real-time, a first graphical interface indicating the first combinatory fitness-athleticism score and a meter that is selected based on an activity type of the second athletic movement;
providing after a specific time frame, second instructions to the user to perform a second athletic movement;
receiving second movement data captured from the sensor during the second athletic movement by the user;
calculating, from the received second movement data, a second combinatory fitness-athleticism score; and
outputting, to the display device and in real-time, a second graphical interface indicating the second combinatory fitness-athleticism score,
wherein the first and second combinatory fitness-athleticism score each comprise a fitness sub-score and a separate athleticism sub-score of the user;
wherein the fitness sub-score is calculated using a first attribute comprising one or more of an endurance fitness attribute, a flexibility fitness attribute and a strength fitness attribute of the user,
wherein at least one of the endurance fitness attribute, the flexibility fitness attribute, and the strength fitness attribute is determined by calculating calories burned during performance by the user, and
wherein the second graphical interface displays a value of the first attribute used to calculate the fitness sub-score.

23. The apparatus of claim 22, wherein the sensor is a first sensor and the apparatus further comprises a second sensor configured to capture movement data and the computer-readable medium further comprises computer-executable instructions that when executed by the processor cause the processor to perform at least: utilizing movement data from the second sensor in the calculation of the first and second combinatory fitness-athleticism scores.

24. The apparatus of claim 22, wherein the value of the first attribute is displayed within a graphical meter that is updated in real-time.

* * * * *

UNITED STATES PATENT AND TRADEMARK OFFICE
CERTIFICATE OF CORRECTION

PATENT NO. : 12,327,624 B2
APPLICATION NO. : 17/737887
DATED : June 10, 2025
INVENTOR(S) : Teresa Aragones et al.

Page 1 of 1

It is certified that error appears in the above-identified patent and that said Letters Patent is hereby corrected as shown below:

In the Claims

Claim 12, Lines 42-44, delete "score and a meter that is selected based on an activity type of the second athletic movement;" and insert --score;--

Claim 12, Line 54, delete "score," and insert --score and a meter that is selected based on an activity type of the second athletic movement,--

Claim 22, Lines 30-32, delete "score and a meter that is selected based on an activity type of the second athletic movement;" and insert --score;--

Claim 22, Line 41, delete "score," and insert --score and a meter that is selected based on an activity type of the second athletic movement,--

Signed and Sealed this
Tenth Day of February, 2026

John A. Squires
*Director of the United States Patent and Trademark Office*